US006541684B1

(12) United States Patent
Bowen et al.

(10) Patent No.: US 6,541,684 B1
(45) Date of Patent: Apr. 1, 2003

(54) NUCLEOTIDE SEQUENCES ENCODING MAIZE RAD51

(75) Inventors: Benjamin A. Bowen, Hayward, CA (US); Mark A. Chamberlin, Windsor Heights; Bruce J. Drummond, Des Moines, both of IA (US); John A. McElver, Durham, NC (US); Rodney J. Rothstein, Maplewood, NJ (US)

(73) Assignees: Trustees of Columbia University in the City of New York, New York, NY (US); Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 09/246,963

(22) Filed: Feb. 9, 1999

Related U.S. Application Data

(60) Provisional application No. 60/074,745, filed on Feb. 13, 1998.

(51) Int. Cl.[7] ................................................. A01H 5/00
(52) U.S. Cl. .................... 800/320.1; 435/69.1; 435/196; 536/23.1; 536/23.5; 536/24.1
(58) Field of Search ............... 536/23.1, 23.5, 536/24.1; 435/410, 468, 196, 69.1; 800/298, 320.1

(56) References Cited

FOREIGN PATENT DOCUMENTS

| WO | WO 93/22443 | 11/1993 |
| WO | WO 97/41228 | 11/1997 |

OTHER PUBLICATIONS

Natalie Teager et al, Isolation and characterization of rad51 orthologs from *Coprinus cinereus* and *Lycopersicon esculentum*, and phylogenetic analysis of eukaryotic recA homologs, Curr Genet 1997, 31: 144–157.*

Kowalczykowski, et al. 1994. Homologous Pairing and DNA Strand–Exchange Proteins. Annu Rev. Biochem. 1994. 63.991–1043.

Sung, 1994. Catalysis of ATP–Dependent Homologous DNA Pairing and Strand Exchange by Yeast RAD51 Protein. Science, vol. 265, 1241–1243.

Stassen, et al. Isolation and characterization of rad51 orthologs from *Coprinus cinereus* and *Lycopersicon esculentum*, and phylogenetic analysis of eukaryotic recA homologs. Curr Genet (1997) 31: 144–157.

Doutriaux, et al. Isolation and characterisation of the RAD51 and DMC1 homologs from *Arabidopsis thaliana*. Mol Gen. Genet (1998) 257: 283–291.

Kanaar and Hoeijmakers, 1998. From competition to collaboration. Nature, vol. 391, 335–338.

Benson, et al. 1998. Synergistic actions of Rad51 and Rad52 in recombination and DNA repair. Nature, vol. 391, 401–404.

Shinohara and Ogawa, 1998. Stimulation by Rad52 of yeast Rad51–mediated recombination. Nature, 391: 404–407.

New, et al., 1998. Rad 52 protein stimulates DNA strand exchange by Rad51 and replication protein A. Nature, 391: 407–410.

Smith, K.N., et al. 1996. Untitled. Embl. Sequence Data Library, XP002105502, Accession No. U43528.

* cited by examiner

*Primary Examiner*—James Ketter
(74) *Attorney, Agent, or Firm*—Foley & Lardner

(57) ABSTRACT

Nucleic acid sequences encoding two RAD51 recombinases active in maize plants are provided. cDNA sequences including the ZmRAD51 coding sequences and unique 3'-untranslated regions which are useful as RFLP probes, are also provided. The production of plasmids containing a nucleic acid sequence encoding a ZmRAD51 fusion protein, as well as the use of the plasmids to introduce the ZmRAD51 coding sequence into a host cell, such as maize cell, are also disclosed.

14 Claims, 3 Drawing Sheets

SEQUENCE LISTING

<160> NUMBER OF SEQ ID NOS: 24

<210> SEQ ID NO 1
<211> LENGTH: 1568
<212> TYPE: DNA
<213> ORGANISM: Zea mays
<220> FEATURE:
<221> NAME/KEY: CDS
<222> LOCATION: (53)...(1072)

<400> SEQUENCE: 1

```
ggcacgagtt cgaacagggg cagaggtgag acttgagaga aggaagaagg tc atg tcg      58
                                                         Met Ser
                                                          1 tcg gcg gcg cag cag cag cag aaa gcg gcg gca gcg gag cag gag gag       106
Ser Ala Ala Gln Gln Gln Gln Lys Ala Ala Ala Ala Glu Gln Glu Glu
        5                  10                  15 gtg gag cac ggg cca ttc ccc atc gag cag ctc cag gct tct gga ata       154
Val Glu His Gly Pro Phe Pro Ile Glu Gln Leu Gln Ala Ser Gly Ile
 20                  25                  30 gct gca ttg gat gtg aag aag ctg aaa gat tct ggt ctc cac act gtg       202
Ala Ala Leu Asp Val Lys Lys Leu Lys Asp Ser Gly Leu His Thr Val
35                  40                  45                  50 gag gct gtg gct tac act cca agg aaa gat ctg cag atc aaa ggg            250
Glu Ala Val Ala Tyr Thr Pro Arg Lys Asp Leu Leu Gln Ile Lys Gly
                55                  60                  65 ata agt gaa gct aaa gct gac aag ata att gaa gca gca tcc aag ata       298
Ile Ser Glu Ala Lys Ala Asp Lys Ile Ile Glu Ala Ala Ser Lys Ile
                70                  75                  80 gtt cca ctg gga ttt aca agt gcc agt caa ctt cat gcg cag cga ctg       346
```

```
                                                            -continued

Val Pro Leu Gly Phe Thr Ser Ala Ser Gln Leu His Ala Gln Arg Leu
        85                  90                  95 gag att att caa gtt aca act gga tca aga gag ctt gat aag ata ttg      394
Glu Ile Ile Gln Val Thr Thr Gly Ser Arg Glu Leu Asp Lys Ile Leu
    100                 105                 110 gag ggt ggg ata gaa aca gga tct atc act gag ata tat ggt gag ttc      442
Glu Gly Gly Ile Glu Thr Gly Ser Ile Thr Glu Ile Tyr Gly Glu Phe
115                 120                 125                 130 cgc tct gga aag act cag ttg tgt cac acc cct tgt gtt aca tgt cag      490
Arg Ser Gly Lys Thr Gln Leu Cys His Thr Pro Cys Val Thr Cys Gln
                135                 140                 145 ctt cca ctg gac cag ggt ggt ggt gaa gga aag gct cta tat att gac      538
Leu Pro Leu Asp Gln Gly Gly Gly Glu Gly Lys Ala Leu Tyr Ile Asp
            150                 155                 160 gca gag ggt aca ttc aga cca caa agg ctc ttg cag att gct gac agg      586
Ala Glu Gly Thr Phe Arg Pro Gln Arg Leu Leu Gln Ile Ala Asp Arg
        165                 170                 175 ttt gga ctg aat ggt gct gat gtg tta gag aat gtg gct tat gcc aga      634
Phe Gly Leu Asn Gly Ala Asp Val Leu Glu Asn Val Ala Tyr Ala Arg
    180                 185                 190 gct tat aat acg gat cat caa tct aga ctt ctg ctg gaa gca gct tcc      682
Ala Tyr Asn Thr Asp His Gln Ser Arg Leu Leu Leu Glu Ala Ala Ser
195                 200                 205                 210 atg atg ata gag acc agg ttt gct ctt atg gtt gta gac agt gcc aca      730
Met Met Ile Glu Thr Arg Phe Ala Leu Met Val Val Asp Ser Ala Thr
                215                 220                 225 gct ctg tac aga act gat ttc tca gga aga ggg gaa cta tca gcg agg      778
Ala Leu Tyr Arg Thr Asp Phe Ser Gly Arg Gly Glu Leu Ser Ala Arg
            230                 235                 240 caa atg cac atg gct aag ttc ctg agg agc ctt cag aag tta gct gat      826
Gln Met His Met Ala Lys Phe Leu Arg Ser Leu Gln Lys Leu Ala Asp
        245                 250                 255 gag ttt gga gta gct gtg gtt atc acc aat caa gta gtg gcc caa gtg      874
Glu Phe Gly Val Ala Val Val Ile Thr Asn Gln Val Val Ala Gln Val
    260                 265                 270 gat gga tct gct atg ttt gct gga ccg cag ttc aag ccc att ggt gga      922
Asp Gly Ser Ala Met Phe Ala Gly Pro Gln Phe Lys Pro Ile Gly Gly
275                 280                 285                 290 aac atc atg gct cat gct tca acc aca agg ctt gct ctt cgc aag ggg      970
Asn Ile Met Ala His Ala Ser Thr Thr Arg Leu Ala Leu Arg Lys Gly
                295                 300                 305 cga ggg gag gaa cgg atc tgt aaa gta ata agc tct ccc tgc ctt gct     1018
Arg Gly Glu Glu Arg Ile Cys Lys Val Ile Ser Ser Pro Cys Leu Ala
            310                 315                 320 gaa gcc gaa gca agg ttt cag tta gct tct gaa ggt att gca gat gtt     1066
Glu Ala Glu Ala Arg Phe Gln Leu Ala Ser Glu Gly Ile Ala Asp Val
        325                 330                 335 aag gat tgagaccata cctgctttac aggcatcttc agatccattg gtctgctatt     1122
Lys Asp
    340 tgctttgtca ttccttgggc caactttcgt gttgcctcac cttgatgtac aaaacggttt     1182 cgttcacata tgtgaatgca cgcctgtgac tgatttaggc gtcctgttgt aaataaaacg     1242 atgcctgttg ccctgttgtg tgttgcatgt aatcgacaac tctacatatc acaattatga     1302 tgtattttag gtttattgt tcgcttagca cagccattgc tggatgtgca atgtgggatt     1362 atagacaaga atccacacaa caacaatggc caatcctgat aaagtagtta gtgacttggg     1422 caaatagcat tgtggtgatc tttgagttca cttgtgataa gaacagggct ggtggctggt     1482
```

-continued

```
ggtgaaaact aacttgtgat cggaacaggt ttaatagga aaactaagga ttctataaaa    1542
aaaaaaataa aaaaaaaaaa aaaaaa                                        1568
```

<210> SEQ ID NO 2
<211> LENGTH: 1020
<212> TYPE: DNA
<213> ORGANISM: Zea mays

<400> SEQUENCE: 2

```
atgtcgtcgg cggcgcagca gcagcagaaa gcggcggcag cggagcagga ggaggtggag     60
cacgggccat tccccatcga gcagctccag gcttctggaa tagctgcatt ggatgtgaag    120
aagctgaaag attctggtct ccacactgtg gaggctgtgg cttacactcc aaggaaagat    180
cttctgcaga tcaaagggat aagtgaagct aaagctgaca agataattga agcagcatcc    240
aagatagttc cactgggatt tacaagtgcc agtcaacttc atgcgcagcg actggagatt    300
attcaagtta caactggatc aagagagctt gataagatat tggagggtgg gatagaaaca    360
ggatctatca ctgagatata tggtgagttc cgctctggaa agactcagtt gtgtcacacc    420
ccttgtgtta catgtcagct tccactggac cagggtggtg gtgaaggaaa ggctctatat    480
attgacgcag agggtacatt cagaccacaa aggctcttgc agattgctga caggtttgga    540
ctgaatggtg ctgatgtgtt agagaatgtg gcttatgcca gagcttataa tacggatcat    600
caatctagac ttctgctgga agcagcttcc atgatgatag agaccaggtt tgctcttatg    660
gttgtagaca gtgccacagc tctgtacaga actgatttct caggaagagg ggaactatca    720
gcgaggcaaa tgcacatggc taagttcctg aggagccttc agaagttagc tgatgagttt    780
ggagtagctg tggttatcac caatcaagta gtggcccaag tggatggatc tgctatgttt    840
gctggaccgc agttcaagcc cattggtgga acatcatgg ctcatgcttc aaccacaagg    900
cttgctcttc gcaagggggcg aggggaggaa cggatctgta agtaataag ctctccctgc    960 cttgctgaag ccgaagcaag gtttcagtta gcttctgaag gtattgcaga tgttaaggat   1020
```

<210> SEQ ID NO 3
<211> LENGTH: 340
<212> TYPE: PRT
<213> ORGANISM: Zea mays

<400> SEQUENCE: 3

```
Met Ser Ser Ala Ala Gln Gln Gln Gln Lys Ala Ala Ala Glu Gln
  1               5                  10                  15

Glu Glu Val Glu His Gly Pro Phe Pro Ile Glu Gln Leu Gln Ala Ser
                 20                  25                  30

Gly Ile Ala Ala Leu Asp Val Lys Lys Leu Lys Asp Ser Gly Leu His
             35                  40                  45

Thr Val Glu Ala Val Ala Tyr Thr Pro Arg Lys Asp Leu Leu Gln Ile
         50                  55                  60

Lys Gly Ile Ser Glu Ala Lys Ala Asp Lys Ile Ile Glu Ala Ala Ser
 65                  70                  75                  80

Lys Ile Val Pro Leu Gly Phe Thr Ser Ala Ser Gln Leu His Ala Gln
                 85                  90                  95

Arg Leu Glu Ile Ile Gln Val Thr Gly Ser Arg Glu Leu Asp Lys
                100                 105                 110

Ile Leu Glu Gly Gly Ile Glu Thr Gly Ser Ile Thr Glu Ile Tyr Gly
            115                 120                 125

Glu Phe Arg Ser Gly Lys Thr Gln Leu Cys His Thr Pro Cys Val Thr
```

-continued

```
            130                 135                 140
Cys Gln Leu Pro Leu Asp Gln Gly Gly Glu Gly Lys Ala Leu Tyr
145                 150                 155                 160

Ile Asp Ala Glu Gly Thr Phe Arg Pro Gln Arg Leu Leu Gln Ile Ala
                165                 170                 175

Asp Arg Phe Gly Leu Asn Gly Ala Asp Val Leu Glu Asn Val Ala Tyr
            180                 185                 190

Ala Arg Ala Tyr Asn Thr Asp His Gln Ser Arg Leu Leu Leu Glu Ala
        195                 200                 205

Ala Ser Met Met Ile Glu Thr Arg Phe Ala Leu Met Val Val Asp Ser
    210                 215                 220

Ala Thr Ala Leu Tyr Arg Thr Asp Phe Ser Gly Arg Gly Glu Leu Ser
225                 230                 235                 240

Ala Arg Gln Met His Met Ala Lys Phe Leu Arg Ser Leu Gln Lys Leu
                245                 250                 255

Ala Asp Glu Phe Gly Val Ala Val Val Ile Thr Asn Gln Val Val Ala
            260                 265                 270

Gln Val Asp Gly Ser Ala Met Phe Ala Gly Pro Gln Phe Lys Pro Ile
        275                 280                 285

Gly Gly Asn Ile Met Ala His Ala Ser Thr Thr Arg Leu Ala Leu Arg
    290                 295                 300

Lys Gly Arg Gly Glu Glu Arg Ile Cys Lys Val Ile Ser Ser Pro Cys
305                 310                 315                 320

Leu Ala Glu Ala Glu Ala Arg Phe Gln Leu Ala Ser Glu Gly Ile Ala
                325                 330                 335

Asp Val Lys Asp
            340
```

<210> SEQ ID NO 4
<211> LENGTH: 461
<212> TYPE: DNA
<213> ORGANISM: Zea mays

<400> SEQUENCE: 4

```
ccatacctgc tttacaggca tcttcagatc cattggtctg ctatttgctt tgtcattcct    60
tgggccaact ttcgtgttgc ctcaccttga tgtacaaaac ggtttcgttc acatatgtga   120
atgcacgcct gtgactgatt taggcgtcct gttgtaaata aaacgatgcc tgttgccctg   180
ttgtgtgttg catgtaatcg acaactctac atatcacaat tatgatgtat tttaggtttt   240
attgttcgct tagcacagcc attgctggat gtgcaatgtg ggattataga caagaatcca   300
cacaacaaca atggccaatc ctgataaagt agttagtgac ttgggcaaat agcattgtgg   360
tgatctttga gttcacttgt gataagaaca gggctggtgg ctggtggtga aaactaactt   420
gtgatcggaa caggtttaat agggaaaact aaggattcta t                      461
```

<210> SEQ ID NO 5
<211> LENGTH: 1574
<212> TYPE: DNA
<213> ORGANISM: Zea mays
<220> FEATURE:
<221> NAME/KEY: CDS
<222> LOCATION: (73)...(1092)

<400> SEQUENCE: 5

```
gaattcggca cgagattttt tgccgcttcg gaggcacctt cgaacaaagc ccaaaagcag    60
ccagcgcacc gc atg tcc tcg tct tcg gcg cac cag aag gcg tcg ccg ccg   111
```

```
                Met Ser Ser Ser Ser Ala His Gln Lys Ala Ser Pro Pro
                  1               5                  10 ata gag gag gaa gcg acg gag cac gga ccc ttc ccc atc gaa cag cta      159
Ile Glu Glu Glu Ala Thr Glu His Gly Pro Phe Pro Ile Glu Gln Leu
         15                  20                  25 cag gca tct gga ata gct gca ctt gat gtg aaa aaa ctc aaa gat gct      207
Gln Ala Ser Gly Ile Ala Ala Leu Asp Val Lys Lys Leu Lys Asp Ala
 30                  35                  40                  45 ggt ctc tgc aca gtg gaa tct gta gca tac tct cca agg aaa gac ctt      255
Gly Leu Cys Thr Val Glu Ser Val Ala Tyr Ser Pro Arg Lys Asp Leu
                 50                  55                  60 ttg caa att aaa ggg att agt gaa gcc aaa gtc gac aag ata att gaa      303
Leu Gln Ile Lys Gly Ile Ser Glu Ala Lys Val Asp Lys Ile Ile Glu
             65                  70                  75 gca gct tcc aag ttg gtt cca ctc gga ttt act agt gct agc caa ctt      351
Ala Ala Ser Lys Leu Val Pro Leu Gly Phe Thr Ser Ala Ser Gln Leu
         80                  85                  90 cat gca cag aga ctt gag atc atc cag ctt aca act gga tct aga gag      399
His Ala Gln Arg Leu Glu Ile Ile Gln Leu Thr Thr Gly Ser Arg Glu
     95                 100                 105 ctt gat caa att ttg gac ggt gga ata gaa aca gga tct atc aca gag      447
Leu Asp Gln Ile Leu Asp Gly Gly Ile Glu Thr Gly Ser Ile Thr Glu
110                 115                 120                 125 atg tat ggt gaa ttt cgc tcc ggg aag act cag ttg tgc cac act ctc      495
Met Tyr Gly Glu Phe Arg Ser Gly Lys Thr Gln Leu Cys His Thr Leu
                130                 135                 140 tgt gtc aca tgt cag ctc cca ttg gac caa ggt ggt ggt gaa gga aag      543
Cys Val Thr Cys Gln Leu Pro Leu Asp Gln Gly Gly Gly Glu Gly Lys
            145                 150                 155 gct ttg tat att gat gca gag ggt aca ttc agg cct caa aga att ctc      591
Ala Leu Tyr Ile Asp Ala Glu Gly Thr Phe Arg Pro Gln Arg Ile Leu
        160                 165                 170 cag ata gca gac agg ttt ggc ttg aat ggc gct gat gta cta gag aat      639
Gln Ile Ala Asp Arg Phe Gly Leu Asn Gly Ala Asp Val Leu Glu Asn
    175                 180                 185 gtg gct tat gcc aga gca tat aac act gat cat caa tca aga ctt ttg      687
Val Ala Tyr Ala Arg Ala Tyr Asn Thr Asp His Gln Ser Arg Leu Leu
190                 195                 200                 205 cta gaa gca gcc tcc atg atg gta gag acc agg ttt gct ctc atg gtt      735
Leu Glu Ala Ala Ser Met Met Val Glu Thr Arg Phe Ala Leu Met Val
                210                 215                 220 gtg gat agt gct aca gcc ctt tac aga act gat ttc tct ggt aga ggg      783
Val Asp Ser Ala Thr Ala Leu Tyr Arg Thr Asp Phe Ser Gly Arg Gly
            225                 230                 235 gag cta tca gca agg cag atg cat ctg gcg aag ttt ctt agg agc ctt      831
Glu Leu Ser Ala Arg Gln Met His Leu Ala Lys Phe Leu Arg Ser Leu
        240                 245                 250 caa aag tta gca gat gag ttt gga gtg gca gtg gta atc acg aac caa      879
Gln Lys Leu Ala Asp Glu Phe Gly Val Ala Val Val Ile Thr Asn Gln
    255                 260                 265 gta gtg gct caa gtg gat ggt gct gca atg ttt gct ggg cca cag atc      927
Val Val Ala Gln Val Asp Gly Ala Ala Met Phe Ala Gly Pro Gln Ile
270                 275                 280                 285 aag ccc att gga ggg aac atc atg gct cat gct tcc aca act agg ctc      975
Lys Pro Ile Gly Gly Asn Ile Met Ala His Ala Ser Thr Thr Arg Leu
                290                 295                 300 ttt ctt cgc aag gga aga ggg gag gag cgg atc tgc aaa gta atc agc     1023
Phe Leu Arg Lys Gly Arg Gly Glu Glu Arg Ile Cys Lys Val Ile Ser
            305                 310                 315
```

```
tct ccc tgc ctg gct gaa gct gaa gca agg ttt cag ata tca tct gag    1071
Ser Pro Cys Leu Ala Glu Ala Glu Ala Arg Phe Gln Ile Ser Ser Glu
    320                 325                 330 ggt gtc act gat gtc aag gac tgaaagcatc ctcatttgca gtccacagca       1122
Gly Val Thr Asp Val Lys Asp
    335                 340 taacttgcca attcagacga atctctgatc tgctgcactc gtgtcggtcc cttgtacaat   1182
caaaatacca gtacaggctt ccagaatgcg aatgcaaatc cgttggagtg tggcactgtc   1242
atcctgttgt ctttaggtac catctaaagt tggcattgtt gtaaagtggt agagcgcaag   1302
gctctacttt gtagccgtgg attcgagccc tatggtgggc gttatttaat ttttttggcg   1362
aaaaagcctt taattgagtt gtttaggtga tatgaataac tctttaggtc atggagttcg   1422
actccatggg agtttaagct gggttaaaaa aaattatggt cacgatcttt ttcacatggg   1482
ctactgtaac atctcgtcta ctcctgaacc gatgttaagc tttttaggac tatagatcat   1542
cttcatatat caacaaaaaa aaaaaaaaaa aa                                 1574
```

<210> SEQ ID NO 6
<211> LENGTH: 1020
<212> TYPE: DNA
<213> ORGANISM: Zea mays

<400> SEQUENCE: 6

```
atgtcctcgt cttcggcgca ccagaaggcg tcgccgccga tagaggagga agcgacggag     60
cacggaccct tccccatcga acagctacag gcatctggaa tagctgcact tgatgtgaaa    120
aaactcaaag atgctggtct ctgcacagtg gaatctgtag catactctcc aaggaaagac    180
cttttgcaaa ttaagggat tagtgaagcc aaagtcgaca agataattga agcagcttcc     240
aagttggttc cactcggatt tactagtgct agccaacttc atgcacagag acttgagatc    300
atccagctta caactggatc tagagagctt gatcaaattt tggacggtgg aatagaaaca    360
ggatctatca cagagatgta tggtgaattt cgctccggga agactcagtt gtgccacact    420
ctctgtgtca catgtcagct cccattggac caaggtggtg gtgaaggaaa ggcttttgtat   480
attgatgcag agggtacatt caggcctcaa agaattctcc agatagcaga caggtttggc    540
ttgaatggcg ctgatgtact agagaatgtg gcttatgcca gagcatataa cactgatcat    600
caatcaagac ttttgctaga agcagcctcc atgatggtag agaccaggtt tgctctcatg    660
gttgtggata tgctacagc cctttacaga actgatttct ctggtagagg ggagctatca    720
gcaaggcaga tgcatctggc gaagtttctt aggagccttc aaaagttagc agatgagttt    780
ggagtggcag tggtaatcac gaaccaagta gtggctcaag tggatggtgc tgcaatgttt    840
gctgggccac agatcaagcc cattggaggg aacatcatgg ctcatgcttc acaactagg    900
ctctttcttc gcaagggaag aggggaggag cggatctgca agtaatcag ctctcctgc     960
ctggctgaag ctgaagcaag gtttcagata tcatctgagg gtgtcactga tgtcaaggac   1020
```

<210> SEQ ID NO 7
<211> LENGTH: 340
<212> TYPE: PRT
<213> ORGANISM: Zea mays

<400> SEQUENCE: 7

```
Met Ser Ser Ser Ala His Gln Lys Ala Ser Pro Pro Ile Glu Glu
  1               5                  10                  15

Glu Ala Thr Glu His Gly Pro Phe Pro Ile Glu Gln Leu Gln Ala Ser
                 20                  25                  30
```

Gly Ile Ala Ala Leu Asp Val Lys Lys Leu Lys Asp Ala Gly Leu Cys
            35                  40                  45

Thr Val Glu Ser Val Ala Tyr Ser Pro Arg Lys Asp Leu Leu Gln Ile
 50                  55                  60

Lys Gly Ile Ser Glu Ala Lys Val Asp Lys Ile Ile Glu Ala Ala Ser
 65                  70                  75                  80

Lys Leu Val Pro Leu Gly Phe Thr Ser Ala Ser Gln Leu His Ala Gln
                 85                  90                  95

Arg Leu Glu Ile Ile Gln Leu Thr Thr Gly Ser Arg Glu Leu Asp Gln
                100                 105                 110

Ile Leu Asp Gly Gly Ile Glu Thr Gly Ser Ile Thr Glu Met Tyr Gly
                115                 120                 125

Glu Phe Arg Ser Gly Lys Thr Gln Leu Cys His Thr Leu Cys Val Thr
130                 135                 140

Cys Gln Leu Pro Leu Asp Gln Gly Gly Gly Glu Gly Lys Ala Leu Tyr
145                 150                 155                 160

Ile Asp Ala Glu Gly Thr Phe Arg Pro Gln Arg Ile Leu Gln Ile Ala
                165                 170                 175

Asp Arg Phe Gly Leu Asn Gly Ala Asp Val Leu Glu Asn Val Ala Tyr
                180                 185                 190

Ala Arg Ala Tyr Asn Thr Asp His Gln Ser Arg Leu Leu Leu Glu Ala
                195                 200                 205

Ala Ser Met Met Val Glu Thr Arg Phe Ala Leu Met Val Val Asp Ser
            210                 215                 220

Ala Thr Ala Leu Tyr Arg Thr Asp Phe Ser Gly Arg Gly Glu Leu Ser
225                 230                 235                 240

Ala Arg Gln Met His Leu Ala Lys Phe Leu Arg Ser Leu Gln Lys Leu
                245                 250                 255

Ala Asp Glu Phe Gly Val Ala Val Ile Thr Asn Gln Val Val Ala
                260                 265                 270

Gln Val Asp Gly Ala Ala Met Phe Ala Gly Pro Gln Ile Lys Pro Ile
            275                 280                 285

Gly Gly Asn Ile Met Ala His Ala Ser Thr Thr Arg Leu Phe Leu Arg
            290                 295                 300

Lys Gly Arg Gly Glu Glu Arg Ile Cys Lys Val Ile Ser Ser Pro Cys
305                 310                 315                 320

Leu Ala Glu Ala Glu Ala Arg Phe Gln Ile Ser Ser Glu Gly Val Thr
                325                 330                 335

Asp Val Lys Asp
            340

<210> SEQ ID NO 8
<211> LENGTH: 458
<212> TYPE: DNA
<213> ORGANISM: Zea mays

<400> SEQUENCE: 8
catcctcatt tgcagtccac agcataactt gccaattcag acgaatctct gatctgctgc      60
actcgtgtcg gtcccttgta caatcaaaat accagtacag gcttccagaa tgcgaatgca     120
aatccgttgg agtgtggcac tgtcatcctg ttgtctttag gtaccatcta agttggcat     180 tgttgtaaag tggtagagcg caaggctcta ctttgtagcc gtggattcga gccctatggt     240
gggcgttatt taattttttt ggcgaaaaag cctttaattg agttgtttag gtgatatgaa     300

```
taactctttta ggtcatggag ttcgactcca tgggagttta agctgggtta aaaaaaatta      360
tggtcacgat ctttttcaca tgggctactg taacatctcg tctactcctg aaccgatgtt      420
aagcttttta ggactataga tcatcttcat atatcaac                              458
```

<210> SEQ ID NO 9
<211> LENGTH: 582
<212> TYPE: DNA
<213> ORGANISM: Zea mays

<400> SEQUENCE: 9

```
ccatacctgc tttacaggca tcttcagatc cattggtctg ctatttgctt tgtcattcct       60
tgggccaact ttcgtgttgc ctcaccttga tgtacaaaac ggtttcgttc acatatgtga      120
atgcacgcct gtgactgatt taggcgtcct gttgtaaata aaacgatgcc tgttgccctg      180
ttgtgtgttg catgtaatcg acaactctac atatcacaat tatgatgtat tttaggtttt      240
attgttcgct tagcacagcc attgctggat gtgcaatgtg ggattataga caagaatcca      300
cacaacaaca atgccaatc ctgataaagt agttagtgac ttgggcaaat agcattgtgg       360
tgatctttga gttcacttgt gataagaaca gggctggtgg ctggtggtga aaactaactt      420
gtgatcggaa caggtttaat agggaaaact aaggattcta taaaaaaaaa aataaaaaaa      480
aaaaaaaaaa actcgagggg gggcccggta cccaattcgc cctatagtga gtgagtcgta      540
ttacaattca ctggccgtcg ttttacaacg tcgtgactgg ga                         582
```

<210> SEQ ID NO 10
<211> LENGTH: 567
<212> TYPE: DNA
<213> ORGANISM: Zea mays

<400> SEQUENCE: 10

```
catcctcatt tgcagtccac agcataactt gccaattcag acgaatctct gatctgctgc       60
actcgtgtcg gtcccttgta caatcaaaat accagtacag gcttccagaa tgcgaatgca      120
aatccgttgg agtgtggcac tgtcatcctg ttgtctttag gtaccatcta agttggcat       180 tgttgtaaag tggtagagcg caaggctcta ctttgtagcc gtggattcga gccctatggt      240
gggcgttatt taattttttt ggcgaaaaag ccttttaattg agttgtttag gtgatatgaa     300
taactcttta ggtcatggag ttcgactcca tgggagttta agctgggtta aaaaaaatta     360
tggtcacgat ctttttcaca tgggctactg taacatctcg tctactcctg aaccgatgtt     420
aagcttttta ggactataga tcatcttcat atatcaacaa aaaaaaaaa aaaaaactcg      480 agggggggcc cggtacccaa ttcgccctat agtgagtgag tcgtattaca attcactggc     540
cgtcgtttta caacgtcgtg actggga                                         567
```

<210> SEQ ID NO 11
<211> LENGTH: 360
<212> TYPE: DNA
<213> ORGANISM: Zea mays

<400> SEQUENCE: 11

```
acattcagac cacaaaggct cttgcagatt gctgacaggt ttggactgaa tggtgctgat       60
gtgttagaga atgtggctta tgccagagct tataatacgg atcatcaatc tagacttctg     120
ctggaagcag cttccatgat gatagagacc aggtttactc ttatggttgt agacagtgcc     180
acagctctgt acagaactga tttctcagga agagggaac tatcagcgag gcaaatgcac      240
atggctaagt tcctgaggag ccttcagaag ttagctgatg agtttggagt agctgtggtt     300
```

-continued

```
atcaccaatc aagtagtggc ccaagtggat ggatctacta tgtttgctgg gccgcagttc    360

<210> SEQ ID NO 12
<211> LENGTH: 38
<212> TYPE: DNA
<213> ORGANISM: Zea mays

<400> SEQUENCE: 12
tatagaattc cacaaaggct cttgcagatt gctgacag                             38

<210> SEQ ID NO 13
<211> LENGTH: 37
<212> TYPE: DNA
<213> ORGANISM: Zea mays

<400> SEQUENCE: 13
atactcgagg cccagcaaac atagtagatc catccac                              37

<210> SEQ ID NO 14
<211> LENGTH: 24
<212> TYPE: DNA
<213> ORGANISM: Zea mays

<400> SEQUENCE: 14
tcccagtcac gacgttgtaa aacg                                            24

<210> SEQ ID NO 15
<211> LENGTH: 36
<212> TYPE: DNA
<213> ORGANISM: Zea mays

<400> SEQUENCE: 15
agcggataac aatttcacac aggaaacagc tatgac                               36

<210> SEQ ID NO 16
<211> LENGTH: 51
<212> TYPE: DNA
<213> ORGANISM: Zea mays

<400> SEQUENCE: 16
gtattgcaga tgttaaggat tgagaccata cctggttaac aggcatctca g              51

<210> SEQ ID NO 17
<211> LENGTH: 27
<212> TYPE: DNA
<213> ORGANISM: Zea mays

<400> SEQUENCE: 17
gcagccaggg atccacatgt cctcgtc                                         27

<210> SEQ ID NO 18
<211> LENGTH: 52
<212> TYPE: DNA
<213> ORGANISM: Zea mays

<400> SEQUENCE: 18
ctgatgtcaa ggactgaaag catcctcatt tgcagttaac agcataactt gc             52

<210> SEQ ID NO 19
<211> LENGTH: 22
<212> TYPE: DNA
<213> ORGANISM: Zea mays
```

-continued

```
<400> SEQUENCE: 19
ccatacctgc tttacaggca tc                                              22

<210> SEQ ID NO 20
<211> LENGTH: 22
<212> TYPE: DNA
<213> ORGANISM: Zea mays

<400> SEQUENCE: 20
catcctcatt tgsagtccac ag                                              22

<210> SEQ ID NO 21
<211> LENGTH: 39
<212> TYPE: DNA
<213> ORGANISM: Artificial Sequence
<220> FEATURE:
<223> OTHER INFORMATION: GFPm to ZmRAD51A fusion, joined by a 6 bp
      linker encoding isoleucine and histidine

<400> SEQUENCE: 21
gacgagctct acaagatcca catgtcgtcg gcggcgcag                            39

<210> SEQ ID NO 22
<211> LENGTH: 12
<212> TYPE: PRT
<213> ORGANISM: Artificial Sequence
<220> FEATURE:
<223> OTHER INFORMATION: protein sequence for GFPm to ZmRAD51A fusion,
      including the isoleucine and histidine linker

<400> SEQUENCE: 22

Asp Glu Leu Tyr Lys Ile His Met Ser Ser Ala Ala
 1               5                  10

<210> SEQ ID NO 23
<211> LENGTH: 39
<212> TYPE: DNA
<213> ORGANISM: Artificial Sequence
<220> FEATURE:
<223> OTHER INFORMATION: GFPm to ZmRAD51B fusion, joined by a 6 bp
      linker encoding isoleucine and histidine

<400> SEQUENCE: 23
gacgagctct acaagatcca catgtcctcg tcttcggcg                            39

<210> SEQ ID NO 24
<211> LENGTH: 13
<212> TYPE: PRT
<213> ORGANISM: Artificial Sequence
<220> FEATURE:
<223> OTHER INFORMATION: protein sequence for GFPm to ZmRAD51B fusion,
      inlcuding isoleucine and histidine linker

<400> SEQUENCE: 24

Asp Glu Leu Tyr Lys Ile His Met Ser Ser Ser Ser Ala
 1               5                  10
```

NUCLEOTIDE SEQUENCES ENCODING MAIZE RAD51

CROSS REFERENCE TO RELATED APPLICATION

This application claims the benefit of U.S. Provisional Application No. 60/074,745, filed Feb. 13, 1998 and is herein incorporated by reference.

BACKGROUND OF THE INVENTION

Transgenic plant product development by conventional transformation and breeding efforts is a slow and unpredictable process. Gene targeting systems can overcome problems with expression variability, unpredictable impacts of random gene insertion on agronomic performance, and the large number of experiments that need to be conducted. Such systems can also provide approaches to manipulating endogeneous genes. Of course, targeting system requires the ability to focus the recombination process to favor recovery of desired targeting events.

The natural cellular DNA repair and recombination machinery consists of a complex array of protein components interacting in a highly controlled manner to ensure that the fidelity of the genome is conserved throughout the many internal events or external stimuli experienced during each cell cycle. The ability to manipulate this machinery requires an understanding of how specific proteins are involved in the process, and how the genes that encode those proteins are regulated. Since the primary approaches to gene targeting involve recombinases, whether operating in their natural in vivo environment (as during normal recombination) or as part of schemes that involve pretreatment of substrates so as to associate DNA with a recombinase and increase efficiency of targeting (e.g., double D-loop), there is a continuing need to isolate and characterize the genes for these molecules. Because many different protein components may be involved in gene targeting, the availability of host-specific genes and proteins could avoid possible problems of incompatibility associated with molecular interactions due to heterologous components.

Sequences for the bacterial RecA recombinase and functional homologs from yeast and several animal species have been disclosed in various publicly accessible sequence databases. Numerous publications characterizing these recombinases exist (see, e.g., Kowalczykowski et al., *Annu. Rev. Biochem.*, 63:991–1043 (1994)). Reports of the use of bacterial RecA in association with DNA sequences to manipulate homologous target DNA, including improvement of the efficiency of gene targeting in non-plant systems, have been published (see, e.g., PCT published Patent Application Nos. WO 87/01730 and WO 93/22443).

The catalysis of in vitro pairing and strand exchange between circular viral single strand DNA ("ss DNA") and linear duplex DNA ("ds DNA") by a RAD51 recombinase from *S. cerevisiae* has also been reported (see, e.g., Sung, *Science*, 265:1241–43 (1994); Kanaar, et al., *Nature* 391:335–338 (1998); Benson, et al. *Nature* 391:401–410 (1998)). To date, work with recombinase enzymes in plants, however, has been very limited. Accordingly, there is an ongoing need for the identification and characterization of the functional activities of recombinase enzymes which may offer improved and expanded methods for use in plant systems, particularly agriculturally important crop species such as maize.

SUMMARY OF THE INVENTION

Polynucleotide sequences, which encode putatively active RAD51 recombinases, have been isolated from maize. Specifically, cDNA clones ZmRAD51A (SEQ ID NOS: 1) and ZmRAD51B (SEQ ID NOS: 5) from a maize tassel library have been identified and sequenced. The cDNA sequences include 3'-untranslated regions (SEQ ID NOS: 4 and 8) suitable for use in making gene-specific probes, e.g., which can be used to map the locus of the respective ZmRAD51 gene in an RFLP map of a maize population. The RFLP probes are typically at least 15 nucleotide residues, although smaller and larger sizes may also be used. The present invention also includes expression cassettes, vectors, and host cells that incorporate the ZmRAD51 genes. Monocot cells, such as maize cells, are particularly preferred as host cells. In addition, a nuclear localization sequence comprising the 5' end of the ZmRAD51 gene is identified.

In a further aspect, the present invention relates to an isolated protein comprising a polypeptide of at least 10 contiguous amino acids encoded by the isolated nucleic acid of ZmRAD51A or ZmRAD51B. In some embodiments, the polypeptide has a sequence selected from the group consisting of SEQ ID NOS: 3 and 7.

In yet another aspect, the present invention relates to a transgenic plant comprising a expression cassette comprising a plant promoter operably linked to any of the isolated nucleic acids of the present invention. Methods for modulating, in a transgenic plant, the expression of the nucleic acids of the present invention are also included. In some embodiments, the transgenic plant is *Zea mays*. The present invention also provides transgenic seed from the transgenic plant.

In a further aspect, the present invention relates to a method of making maize recombinase by transforming or transfecting a host cell with an expression vector containing one of the isolated nucleic acids of the present invention and purifying the recombinase protein from the host cell. In some embodiments, the host cell is a bacterial cell, a yeast cell, or a plant cell.

DETAILED DESCRIPTION OF THE INVENTION

Figure 1:
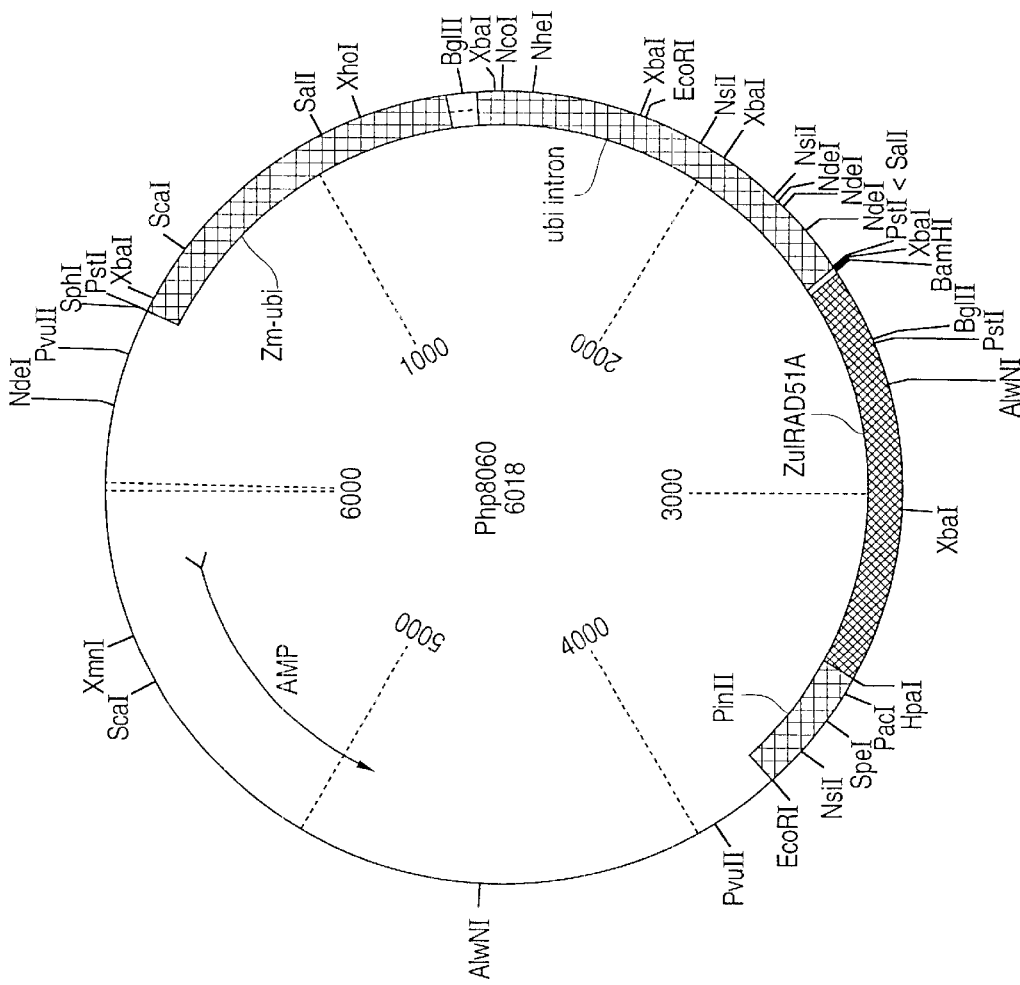
FIG. 1 shows a map of a plasmid designated PHP8060 derived from the insertion of a modified ZmRAD51A gene between a maize ubiquitin promoter and a potato proteinase inhibitor ("PinII") terminator in a pUC19 plasmid backbone.

Full-length cDNA clones for two maize homologs of the yeast RAD51 gene have been isolated. Significant transcription levels have been detected primarily in immature ears and anthers that contain cells progressing through the early stages of meiosis. The two isolated cDNAs, however, are more closely related to RAD51 family members expressed in mitotic cells than to the meiosis-specific homologs from plants (LIM15) and yeast (DMC1). RFLP mapping indicates that the *Zea mays* genome contains two genes encoding different variants of the ZmRAD51 recombinase enzyme. The genes encoding each protein (ZmRAD51A and ZmRAD51B) are unlinked, and their map positions do not correspond to any known maize mutations with a meiotic phenotype. In addition to providing nucleotide sequences, which can be used to produce substantially purified RAD51 proteins, the results presented herein indicate that sequences from the ZmRAD51A and ZmRAD51B cDNA clones can serve both as sources of hybridization probes for RAD51-related genes, as well as novel and unique RFLP probes for applications such as mapping or marker-assisted selection in maize.

The isolated polynucleotides and polypeptides of the present invention can be used over a broad range of plant types, particularly monocots such as the species of the family Gramineae including Hordeum, Secale, Triticum, Sorghum (e.g., S. bicolor) and Zea (e.g., Z. mays). The isolated nucleic acid and proteins of the present invention can also be used in species from the genera: Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, and Avena.

Nucleotide Sequence Encoding ZmRAD51A & ZmRAD51B Proteins

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning—A Laboratory Manual*, 2nd ed., Vol. 1–3 (1989); and *Current Protocols in Molecular Biology*, F. M. Ausubel et al., Eds., Current Protocols, a joint venture between Greene Publishing Associates, Inc. and John Wiley & Sons, Inc. (1994).

The terms "isolated" refers to material, such as nucleic acid or protein, which is: (1) substantially or essentially free from components that normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by means of human intervention performed within the cell from which it originates. See, e.g., Compound and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids, which are "isolated" as defined herein, are also referred to as "heterologous" nucleic acids.

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Further, this invention contemplates the use of both the methionine-containing and the methionine-less amino terminal variants of the protein of the invention.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.* 2: 482 (1981); by the homology alignment algorithm of Needleman and Wunsch, *J. Mol. Biol.* 48: 443 (1970); by the search for similarity method of Pearson and Lipman, *Proc. Natl. Acad. Sci.* 85: 2444 (1988); by computerized implementations of these algorithms, including, but not limited to: CLUSTAL in the PC/Gene program by Intelligenetics, Mountain View, Calif., GAP, BESTFIT, BLAST,, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73: 237–244 (1988); Higgins and Sharp, *CABIOS* 5: 151–153 (1989); Corpet, et al., *Nucleic Acids Research* 16: 10881–90 (1988); Huang, et al., *Computer Applications in the Biosciences* 8: 155–65 (1992), and Pearson, et al., *Methods in Molecular Biology* 24: 307–331 (1994); preferred computer alignment methods also include the BLASTP, BLASTN, and BLASTX algorithms. Altschul, et al., *J. Mol. Biol.* 215: 403–410 (1990). Alignment is also often performed by inspection and manual alignment.

Unless otherwise stated, sequence identity/similarity values provided herein refer to the value obtained using the BLAST 2.0 suite of programs using default parameters. Altschul et al., *Nucleic Acids Res.* 25:3389–3402 (1997). Software for performing BLAST analyses is publicly available, e.g., through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149–163 (1993)) and XNU (Claverie and States, *Comput. Chem.*, 17:191–201 (1993)) low-complexity filters can be employed alone or in combination.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer *Applic. Biol. Sci.,* 4: 11–17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) (i) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, more preferably at least 70%, 80%, 90%, and most preferably at least 95%. Polypeptides which are "substantially similar" share sequences as noted above except that residue positions which are not identical may differ by conservative amino acid changes.

Another indication that nucleotide sequences are substantially identical is if two molecules hybridize to each other under stringent conditions. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code. One indication that two nucleic acid sequences are substantially identical is that the polypeptide, which the first nucleic acid encodes, is immunologically cross reactive with the polypeptide encoded by the second nucleic acid.

(e) (ii) The terms "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch, *J. Mol. Biol.* 48: 443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

The terms "stringent conditions" or "stringent hybridization conditions" includes reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.,* 138:267–284 (1984): $T_m=81.5°$ C.+16.6 (log M)+0.41 (%GC)–0.61 (% form)–500/L; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with $\geq 90\%$ identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes,* Part I, Chapter 2 "Overview of principles of hybridization and the strategy of nucleic acid probe assays", Elsevier, N.Y. (1993); and *Current Protocols in Molecular*

*Biology*, Chapter 2, Ausubel, et al., Eds., Greene Publishing and Wiley-Interscience, New York (1995).

The present invention provides isolated nucleic acids comprising polynucleotides complementary to the polynucleotides of the ZmRAD51 polynucleotides. As those of skill in the art will recognize, complementary sequences base-pair throughout the entirety of their length with the polynucleotides (i.e., have 100% sequence identity over their entire length). Complementary bases associate through hydrogen bonding in double stranded nucleic acids. For example, the following base pairs are complementary: guanine and cytosine; adenine and thymine; and adenine and uracil.

The present invention provides isolated nucleic acids comprising polynucleotides of the present invention, wherein the polynucleotides encode a protein having a subsequence of contiguous amino acids from a polypeptide of the present invention. The length of contiguous amino acids from the prototype polypeptide is selected from the group of integers consisting of from at least 10 to the number of amino acids within the prototype sequence. Thus, for example, the polynucleotide can encode a polypeptide having a subsequence having at least 10, 15, 20, 25, 30, 35, 40, 45, or 50, contiguous amino acids from the prototype polypeptide.

The present invention provides subsequences comprising isolated nucleic acids containing at least 15 contiguous bases of the inventive sequences. The number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, or 200 nucleotides. Subsequences of the isolated nucleic acid can be used to modulate or detect gene expression by introducing into the subsequences compounds which bind, intercalate, cleave and/or crossling to nucleic acids. Exemplary compounds include acridine, psoralen, phenanthroline, naphthoquinone, daunomycin or chloroethylaminoaryl conjugates. The subsequences of the present invention can comprise structural characteristics of the sequence from which it is derived. Alternatively, the subsequences can lack certain structural characterisitics of the larger sequence from which it is derived such as a poly(A) tail.

The proteins encoded by polynucleotides of this embodiment, when presented as an immunogen, elicit the production of polyclonal antibodies which specifically bind to a prototype polypeptide such as the ZmRAD51 polypeptides. Generally, however, a protein encoded by a polynucleotide of this embodiment does not bind to antisera raised against the prototype polypeptide when the antisera has been fully immunosorbed with the prototype polypeptide. Methods of making and assaying for antibody binding specificity/affinity are well known in the art Exemplary immunoassay formats include ELISA, competitive immunoassays, radioimmunoassays, Western blots, indirect immunofluorescent assays and the like.

Nucleotide sequences encoding ZmRAD51 have now been determined by methods described more fully in the Examples below. Briefly, DNA encoding ZmRAD51 was obtained by screening a maize tassel library with a 360 bp probe isolated using a set of degenerate PCR primers designed from known RAD51 consensus sequences. The nucleic acid sequences and the corresponding deduced amino acid sequences for the two ZmRAD51 recombinases are shown below in Tables I (SEQ ID NO: 1) and II (SEQ ID NO: 5).

Tables I and II disclose the full nucleotide sequence of the cDNA clones for ZmRAD51A and ZmRAD51B, respectively. The ATG start of translation in each case is indicated in bold, as is the TGA translation stop codon. Both genes are 1020 nucleotides long, coding for polypeptides of 340 amino acids. The two maize genes exhibit substantial identity with each other, primarily in the coding portion; however they do diverge in sequence in the untranslated regions, a feature that allowed the identification of unique sequences suitable for making gene-specific PCR probes. In comparison to the other RAD51 genes, similarity is also high with the reported tomato sequence. This similarity, except for conserved regions, decreases when comparisons are made to the animal RAD51 genes. Table V compares the actual % similarity and % identity in the polypeptide sequences among the different genes. The two maize RAD51 recombinases are over 94% similar to each other and 90% identical in the coding portions. Very similar values are observed when the maize polypeptide sequences are compared to tomato RAD51. The similarity drops to about 82% and identity to about 69% when comparing the two maize RAD51 recombinases to animal RAD51 recombinase sequences.

The two cloned maize cDNAs offer both conserved sequences that can be used to recover other RAD51 related genes, as well as unique sequences suitable for generating gene- or sequence-specific probes. The two ZmRAD51 cDNAs were cloned into vectors and unique PCR amplified fragments were subsequently mapped along with an assortment of other RFLP probes onto previously constructed maize RFLP maps using different populations generated for this purpose. The vector PHP8057 contains the ZmRAD51A cDNA cloned into pBlueScript™ vector. The vector PHP8058 contains the ZmRAD51B cDNA cloned into pBlueScrip™. The specific sequences that were PCR amplified from vectors PHP8057 and PHP8058 and used as fragment probes for the mapping work are shown in Tables III (SEQ ID NO: 9) and IV (SEQ ID NO: 10). Only the sense strands are shown in these Tables. The regions corresponding to primers PHN10664 (5' primer for RAD51A, SEQ ID NO: 19), PHN10665 (5' primer for RAD51B, SEQ ID NO: 20), and the sequence complement of PHN162 (3' primer for both) are underlined in the Tables.

The ZmRAD51A gene was mapped in a MARSA (Marker Assisted Recombinant Selection A population) F4 population generated from crosses of maize lines R03×N46. In the RFLP map of the MARSA population, the ZmRAD51A gene mapped to chromosome 7, about 40% down the length of the linkage group. In the RFLP map of the ALEB9 population, ZmRAD51B maps on chromosome 3, about 25% down the length of this linkage group. Each of the clone fragments mapped to a single locus making them useful reference markers for those positions on the linkage groups.

Redundancy in the genetic code permits variation in the gene sequences shown in Table I and Table II. In particular, one skilled in the art will recognize specific codon preferences by a specific host species and can adapt the disclosed sequence as preferred for a desired host. For example, preferred codon sequences typically have rare codons (i.e., codons having a usage frequency of less than about 20% in known sequences of the desired host) replaced with higher frequency codons. Codon preferences for a specific organism may be calculated, for example, by utilizing codon usage tables available on the INTERNET. Codon usage in the coding regions of the polynucleotides of the present invention can be analyzed statistically using commercially available software packages such as "Codon Preference"

available from the University of Wisconsin Genetics Computer Group (see Devereaux et al., *Nucleic Acids Res.* 12: 387–395 (1984)) or MacVector 4.1 (Eastman Kodak Co., New Haven, Conn.). Thus, the present invention provides a codon usage frequency characteristic of the coding region of at least one of the polynucleotides of the present invention. The number of polynucleotides that can be used to determine a codon usage frequency can be any integer from 1 to the number of polynucleotides of the present invention as provided herein. Optionally, the polynucleotides will be full-length sequences. An exemplary number of sequences for statistical analysis can be at least 1, 5, 10, 20, 50, or 100. Nucleotide sequences which have been optimized for a particular host species by replacing any codons having a usage frequency of less than about 20% are referred to herein as "codon optimized sequences."

Additional sequence modifications are known to enhance protein expression in a cellular host. These include elimination of sequences encoding spurious polyadenylation signals, exon/intron splice site signals, transposon-like repeats, and/or other such well-characterized sequences which may be deleterious to gene expression. The GC content of the sequence may be adjusted to levels average for a given cellular host, as calculated by reference to known genes expressed in the host cell. Where possible, the sequence may also be modified to avoid predicted hairpin secondary mRNA structures. Other useful modifications include the addition of a translational initiation consensus sequence at the start of the open reading frame, as described in Kozak, *Mol. Cell Biol.*, 9:5073–5080 (1989). Nucleotide sequences which have been optimized for expression in a given host species by elimination of spurious polyadenylation sequences, elimination of exon/intron splicing signals, elimination of transposon-like repeats and/or optimization of GC content in addition to codon optimization are referred to herein as an "expression enhanced sequence."

More effective variants of RAD51A or RAD51B could be synthesized through the use of in vitro recombination (Zhang, J.-H., G. Dawes, W. P. C. Stemmer. 1997. Directed evolution of a fucosidase from a galactosidase by DNA shuffling and screening. Proc. Natl. Acad. Sci. USA 94:4504–4509). For example, the RAD51A and RAD51B from maize and other species could be recombined using the method of DNA shuffling and screened or selected for more effective variants.

In addition, the native ZmRAD51 gene or a modified version of the ZmRAD51 gene could be further optimized for expression by omitting the predicted signal and pre-sequence, replacing the signal sequence with another signal sequence, or replacing the signal and pre-sequence with another type of targeting or localization sequence. The ZmRAD51 nuclear localization sequence is located within in the 5' end of the coding region, preferably the first 40 amino acids of sequence SEQ ID NO: 3 or 7, more preferably the first 30 amino acids of SEQ ID NO: 3 or 7, even more preferably the first 20 amino acids of SEQ ID NO: 3 or 7 or most preferably the first 10 amino acids. The corresponding polynucleotide sequence would be from nucleotide 53 to 113 of SEQ ID NO: 1 or nucleotide 73 to 132 of SEQ ID NO: 5 and fragments thereof.

Proteins

The isolated proteins of the present invention comprise a polypeptide having at least 10 amino acids encoded by any one of the polynucleotides of the present invention as discussed more fully, above, or polypeptides which are conservatively modified variants thereof. The proteins of the present invention or variants thereof can comprise any number of contiguous amino acid residues from a polypeptide of the present invention, wherein that number is selected from the group of integers consisting of from 10 to the number of residues in a full-length polypeptide of the present invention. Optionally, this subsequence of contiguous amino acids is at least 15, 20, 25, 30, 35, or 40 amino acids in length, often at least 50, 60, 70, 80, or 90 amino acids in length. Further, the number of such subsequences can be any integer selected from the group consisting of from 1 to 20, such as 2, 3, 4, or 5.

As those of skill will appreciate, the present invention includes catalytically active polypeptides of the present invention (i.e., enzymes). Catalytically active polypeptides have a specific activity of at least 20%, 30%, or 40%, and preferably at least 50%, 60%, or 70%, and most preferably at least 80%, 90%, or 95% that of the native (non-synthetic), endogenous polypeptide. Further, the substrate specificity ($K_{cat}/K_m$) is optionally substantially similar to the native (non-synthetic), endogenous polypeptide. Typically, the $K_m$ will be at least 30%, 40%, or 50%, that of the native (non-synthetic), endogenous polypeptide; and more preferably at least 60%, 70%, 80%, or 90%. Methods of assaying and quantifying measures of enzymatic activity and substrate specificity ($k_{cat}/K_m$), are well known to those of skill in the art.

Generally, the proteins of the present invention will, when presented as an immunogen, elicit production of an antibody specifically reactive to a polypeptide of the present invention. Further, the proteins of the present invention will not bind to antisera raised against a polypeptide of the present invention which has been fully immunosorbed with the same polypeptide. Innunoassays for determining binding are well known to those of skill in the art. A preferred immunoassay is a competitive immunoassay as discussed, infra. Thus, the proteins of the present invention can be employed as immunogens for constructing antibodies immunoreactive to a protein of the present invention for such exemplary utilities as immunoassays or protein purification techniques.

Modulating Polypeptide Levels and/or Composition

The present invention further provides a method for modulating (i.e., increasing or decreasing) the concentration or composition of the polypeptides of the present invention in a plant or part thereof. Modulation can be effected by increasing or decreasing the concentration and/or the composition (i.e., the ratio of the polypeptides of the present invention) in a plant. The method comprises introducing into a plant cell an expression cassette comprising a polynucleotide of the present invention as described above to obtain a transformed plant cell, culturing the transformed plant cell under plant cell growing conditions, and inducing or repressing expression of a polynucleotide of the present invention in the plant for a time sufficient to modulate concentration and/or composition in the plant or plant part.

In some embodiments, the content and/or composition of polypeptides of the present invention in a plant may be modulated by altering, in vivo or in vitro, the promoter of a gene to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., PCT/US93/03868. And in some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate the concentration and/or composition of polypeptides of the present invention in the plant. Plant forming conditions are well known in the art and discussed briefly, supra.

In general, concentration or composition is increased or decreased by at least 5%, 10%, 20%, 30%, 40%, 50%, 60%, 70%, 80%, or 90% relative to a native control plant, plant part, or cell lacking the aforementioned expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds, which activate expression from these promoters, are well known in the art. In preferred embodiments, the polypeptides of the present invention are modulated in monocots, particularly maize.

Molecular Markers

The present invention provides a method of genotyping a plant comprising a RAD51 polynucleotide. Preferably, the plant is a monocot, such as maize or sorghum. Genotyping provides a means of distinguishing homologs of a chromosome pair and can be used to differentiate segregants in a plant population.

Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual,* Chapter 7, Clark, Ed., Springer-Verlag, Berlin (1997). For molecular marker methods, see generally, The DNA Revolution by Andrew H. Paterson 1996 (Chapter 2) in: Genome Mapping in Plants (ed. Andrew H. Paterson) by Academic Press/R. G. Landis Company, Austin, Tex., pp.7–21.

The particular method of genotyping in the present invention may employ any number of molecular marker analytic techniques such as, but not limited to, restriction fragment length polymorphisms (RFLPs). RFLPs are the product of allelic differences between DNA restriction fragments caused by nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed. Differences in fragment size among alleles represent an RFLP. Thus, the present invention further provides a means to follow segregation of RAD51 genes of the present invention as well as chromosomal sequences genetically linked to RAD51 genes using such techniques as RFLP analysis. Linked chromosomal sequences are within 50 centiMorgans (cM), often within 40 or 30 cM, preferably within 20 or 10 cM, more preferably within 5, 3, 2, or 1 cM of a RAD51 gene of the present invention.

In the present invention, the nucleic acid probes employed for molecular marker mapping of plant nuclear genomes selectively hybridize, under selective hybridization conditions, to a gene encoding a RAD51 polynucleotide. In preferred embodiments, the probes are selected from RAD51 polynucleotides. Typically, these probes are cDNA probes or Pst I genomic clones. In the present invention probes can be made from the polynucleotide sequences found in Table III (SEQ ID NO:9), Table IV (SEQ ID NO: 10), or SEQ ID NO:11. The length of RAD51 probes are typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome complement. Some exemplary restriction enzymes employed in RFLP mapping are EcoRI, EcoRv, and SstI. As used herein the term "restriction enzyme" includes reference to a composition that recognizes and, alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a RAD5 polynucleotide sequence of said genomic DNA; (c) detecting therefrom a RFLP.

Other methods of differentiating polymorphic (allelic) variants of the polynucleotides of the present invention can be had by utilizing molecular marker techniques well known to those of skill in the art including such techniques as: 1) single stranded conformation analysis (SSCP); 2) denaturing gradient gel electrophoresis (DGGE); 3) RNase protection assays; 4) allele-specific oligonucleotides (ASOs); 5) the use of proteins which recognize nucleotide mismatches, such as the *E. coli* mutS protein; and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Thus, the present invention further provides a method of genotyping comprising the steps of contacting, under stringent hybridization conditions, a sample suspected of comprising a RAD51 polynucleotide with a nucleic acid probe. Generally, the sample is a plant sample; preferably, a sample suspected of comprising a maize RAD5 polynucleotide (e.g., gene, mRNA). The nucleic acid probe selectively hybridizes, under stringent conditions, to a subsequence of a RAD51 polynucleotide comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a RAD51 polynucleotide.

Expression of Proteins in Host Cells

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made. A review of expression systems can be found in *Recombinant Gene Expression Protocols,* Tuan, Ed., Humana Press, New Jersey (1997).

In brief summary, the expression of isolated nucleic acids encoding a protein of the present invention will typically be achieved by operably linking, for example, the DNA or cDNA to a promoter (which is either constitutive, cell and/or tissue specific, or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation, and a transcription/translation terminator. One of skill would recognize that modifications can be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

A. Expression in Prokaryotes

Prokaryotic cells may be used as hosts for expression. Prokaryotes most frequently are represented by various strains of *E. coli;* however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang et al., Nature 198:1056 (1977)), the tryptophan (trp) promoter system (Goeddel et al., Nucleic Acids Res. 8:4057 (1980)) and the lambda derived P L promoter and N-gene ribosome binding site (Shimatake et al., Nature 292:128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using Bacillus sp. and Salmonella (Palva, et al., Gene 22: 229–235 (1983); Mosbach, et al., Nature 302: 543–545 (1983)).

B. Expression in Eukaryotes

A variety of eukaryotic expression systems such as yeast, insect cell lines, plant and mammalian cells, are known to those of skill in the art. As explained briefly below, a protein of the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, F., et al., *Methods in Yeast Genetics,* Cold Spring Harbor Laboratory (1982) is a well recognized work describing the various methods available to produce the protein in yeast. Suitable vectors usually have expression control sequences, such as promoters, including 3-phosphoglycerate kinase or other glycolytic enzymes, and an origin of replication, termination sequences and the like as desired. For instance, suitable vectors are described in the literature (Botstein, et al., Gene 8: 17–24 (1979); Broach, et al., Gene 8: 121–133 (1979)).

A protein of the present invention, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect, or plant origin. Illustrative of cell cultures useful for the production of the peptides are mammalian cells. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen et al., *Immunol. Rev.* 89: 49 (1986)), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection Catalogue of Cell Lines and Hybridomas (7th edition, 1992).

Appropriate vectors for expressing proteins of the present invention in insect cells are usually derived from the SF9 baculovirus. Suitable insect cell lines include mosquito larvae, silkworm, armyworm, moth and Drosophila cell lines such as a Schneider cell line (See Schneider, *J. Embryol. Exp. Morphol.* 27: 353–365 (1987).

As with yeast, when higher animal or plant host cells are employed, polyadenlyation or transcription terminator sequences are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, et al., *J. Virol.* 45: 773–781 (1983)). Additionally, gene sequences to control replication in the host cell may be incorporated into the vector such as those found in bovine papilloma virus type-vectors. Saveria-Campo, M., Bovine Papilloma Virus DNA a Eukaryotic Cloning Vector in *DNA Cloning Vol. II a Practical Approach,* D. M. Glover, Ed., IRL Press, Arlington, Va. pp. 213–238 (1985).

Gene Delivery

An isolated maize RAD51 recombinase gene may be incorporated into a plasmid and introduced into a host cell, e.g., a heterologous non-maize cell. Expression of the recombinant ZmRAD51 protein encoded by one of the nucleotide sequences disclosed herein can provide a source of a substantially pure plant recombinase.

A polynucleotide sequence encoding for ZmRAD51A (SEQ ID NO:2) or ZmRAD51B (SEQ ID NO:6) may be delivered to a host cell such as a plant cell for transient transformation or stable integration into the plant's genome by methods known in the art. Preferably, the host cell is a plant cell and, more preferably, a monocot cell, such as a maize cell. To accomplish such delivery, a nucleotide sequence containing the coding sequence for ZmRAD51A (SEQ ID NO:2) or the coding sequence for ZmRAD51B (SEQ ID NO:6) may be attached to regulatory elements needed for the expression of the gene in a particular host cell or system. These regulatory elements include, for example, promoters, terminators, and other elements that permit desired expression of the enzyme in a particular plant host, in a particular tissue or organ of a host such as vascular tissue, root, leaf, or flower, or in response to a particular signal. These regulatory elements may also include the native regulatory sequences normally associated with the RAD51 genes in their endogenous state.

Promoters

A promoter is a DNA sequence that directs the transcription of a structural gene, e.g., that portion of the DNA sequence that is transcribed into messenger RNA (mRNA) and then translated into a sequence of amino acids characteristic of a specific polypeptide. Typically, a promoter is located 5' of the structural gene it controls, proximal to the transcriptional start site. A promoter may be inducible (or derepressible), increasing the rate of transcription in response to the presence or absence of a resulting agent. In contrast, a promoter may be constitutive, whereby the rate of transcription is not regulated by a specific agent. A promoter may be regulated in a tissue-specific or tissue-preferred manner, such that it is only active in transcribing the operably linked coding region in a specific tissue type or types, such as plant leaves, roots, or meristem. Examples of suitable promoters which may be operably linked to the present ZmRAD51 coding sequences include the maize ubiquitin promoter ubiquitin (Christensen et al., *Plant Mol. Biol.*, 12:619–632 (1992) and the ZmDJ1 promoter (Baszczynski et al., *Maydica*, 42:189–201 (1997)).

Inducible Promoters

An inducible promoter useful in the present invention may be operably linked to a nucleotide sequence encoding ZmRAD51. Optionally, the inducible promoter is operably linked to a nucleotide sequence encoding a signal sequence which is operably linked to a nucleotide sequence encoding ZmRAD51. With an inducible promoter, the rate of transcription increases in response to an inducing agent. Any inducible promoter can be used in the present invention to direct transcription of ZmRAD51, including those described in Ward et al., *Plant Molecular Biol.*, 22: 361:–366 (1993). Exemplary inducible promoters include that from the ACE1 system which responds to copper (Mett et al., *Proc. Nat'l Acad. Sci.* (*U.S.A.*) *NAS,* 90: 4567–4571(1993)); the In 2 gene promoter from maize which responds to benzenesulfonamide herbicide safeners (Hershey and Stoner, *Plant Mol. Biol.*, 17:679–690 (1991)); and the Tet repressor from Tn10 (Hershey, *Mol. Gen. Genetics,* 227:229–237 (1991)).

A particularly preferred inducible promoter is one that responds to an inducing agent to which plants do not normally respond. One example of such a promoter is the steroid hormone gene promoter. Transcription of the steroid hormone gene promoter is induced by a glucocorticosteroid hormone. (Schena et al., *Proc. Nat'l. Acad. Sci.* (*U.S.A.*)., 88:10421 (1991)).

The present invention also provides an expression vector having an inducible promoter operably linked to a nucleotide sequence encoding ZmRAD51. The expression vector may be introduced into plant cells and the cells exposed to an inducer of the inducible promoter. The cells may then be screened for the presence of ZmRAD51 protein by immunoassay methods.

Tissue-specific or Tissue-Preferred Promoters

An expression vector of the present invention may include a tissue-specific or tissue-preferred promoter operably linked to the nucleotide sequence encoding ZmRAD51. The expression vector is introduced into plant cells. The cells may be screened for the presence of ZmRAD51 protein, e.g., by immunological methods.

Optionally, the tissue-preferred promoter is operably linked to a nucleotide sequence encoding a signal sequence which is operably linked to a nucleotide sequence encoding ZmRAD51. Plants transformed with a gene encoding ZmRAD51 operably linked to a tissue specific promoter produce ZmRAD51 protein at least preferentially and, preferably, exclusively ("tissue-specific promoter") in a specific tissue.

Any tissue-specific or tissue-preferred promoter can be utilized in the instant invention. Examples of such promoters include a root-preferred promoter such as that from the phaseolin gene as described in Sengupta-Gopalan et al., *Proc. Nat'l, Acad. Sci.* (*U.S.A.*), 82:3320–3324 (1985) or the TobRB7 gene characterized by Yamamoto et al, *Plant Cell,* 3:371–382 (1991); a leaf-specific and light-induced promoter such as that from cab or rubisco as described in Simpson et al., *EMBO J.,* 4(11):2723–2729 (1985); an anther-specific promoter such as that from LAT52 as described in Twell et al., *Mol. Gen. Genet.,* 217:240–245 (1989); a pollen-specific promoter such as that from Zm13 as described in Guerrero et al., *Mol. Gen. Genet.,* 224:161–168 (1993); and a microspore-preferred promoter such as that from apg as described in Twell et al., *Sex. Plant Reprod.,* 6:217–224 (1993).

Other tissue-specific promoters useful in the present invention include a phloem-preferred promoter such as that associated with the Arabidopsis sucrose synthase gene as described in Martin et al., 1993, *The Plant Journal* 4:367–377; a floral-specific promoter such as that of the Arabidopsis HSP 18.2 gene described in Tsukaya et al., *Mol. Gen. Genet.,* 237:26–32 (1993) and of the Arabidopsis HMG2 gene as described in Enjuto et al., *Plant Cell,* 7:517–527 (1995).

Constitutive Promoters

Alternatively, the nucleotide sequence encoding ZmRAD51 may be operably linked to a constitutive promoter. Optionally, the constitutive promoter is operably linked to a nucleotide sequence encoding a signal sequence which is operably linked to a nucleotide sequence encoding ZmRAD51. Many different constitutive promoters can be utilized in the instant invention to express ZmRAD51. Examples include promoters from plant viruses such as the 35S promoter from cauliflower mosaic virus (CaMV), as described in Odell et al., *Nature,* 313:810–812 (1985), and promoters from genes such as rice actin (McElroy et al., *Plant Cell,* 2:163–171 (1990)); ubiquitin (Christensen et al., *Plant Mol. Biol.,* 12:619–632 (1992); pEMU (Last et al., *Theor. Appl. Genet.,* 81:581–588 (1991)); MAS (Velten et al., *EMBO J.,* 3:2723–2730 (1984)); and maize H3 histone (Lepetit et al., *Mol. Gen. Genet.,* 231:276–285 (1992)).

Additional Regulatory Elements

Additional regulatory elements that may be connected to the ZmRAD51 nucleic acid sequence for expression in plant cells include terminators, polyadenylation sequences, and nucleic acid sequences encoding signal peptides that permit localization within a plant cell or secretion of the protein from the cell. Such regulatory elements and methods for adding or exchanging these elements with the regulatory elements of the ZmRAD51 gene are known, and include, but are not limited to, 3'termination and/or polyadenylation regions such as those of the *Agrobacterium tumefaciens* nopaline synthase (nos) gene (Bevan et al., *Nucl. Acids Res.*, 12:369–385 (1983)); the potato proteinase inhibitor II (PinII) gene (Keil et al., *Nucl. Acids Res.*, 14:5641–5650 (1986)); and the CaMV 19S gene (Mogen et al., *Plant Cell*, 2:1261–1272 (1990)).

Plant signal sequences, including, but not limited to, signal-peptide encoding DNA/RNA sequences which target proteins to the extracellular matrix of the plant cell (Dratewka-Kos et al., *J. Biol. Chem.*, 264:48964900 (1989)) and the *Nicotiana plumbaginifolia* extensin gene (DeLoose et al., *Gene*, 99:95–100 (1991)), or signal peptides which target proteins to the vacuole like the sweet potato sporamin gene (Matsuka et al., *Proc. Nat'l. Acad. Sci. (U.S.A.)*, 88:834 (1991)) and the barley lectin gene (Wilkins et al., *Plant Cell*, 2:301–313 (1990)), or signals which cause proteins to be secreted such as that of PRIb (Lind et al., *Plant Mol. Biol.*, 18:47–53 (1992)), or those which target proteins to the plastids such as that of rapeseed enoyl-ACP reductase (Verwaert et al., *Plant Mol. Biol.*, 26:189–202 (1994)) are useful in the invention.

Another regulatory element that may be employed in combination with the ZmRAD51 nucleic acid sequence for expression in plant cells is a nuclear localization sequence ("NLS") which directs localization of expression of the ZmRAD51 protein to the nucleus of a plant cell. Examples of suitable nuclear localization sequences may be found in Kalderon et al., *Cell*, 39:499–509 (1984) and Hicks et al., *Plant Cell*, 5:983–994 (1993). Alternatively, the native ZmRAD51 nuclear localization signal located in the 5' region of the coding sequence, most preferably from nucleotide 53 to 113 of SEQ ID NO: 1 or nucleotide 73 to 132 of SEQ ID NO:5 could be used.

Gene Delivery Methods

Numerous methods for introducing foreign genes into plant cells are known and can be used to insert a ZmRAD51 gene into a plant host cell, including biological and physical DNA delivery protocols. See, for example, Miki et al., "Procedure for Introducing Foreign DNA into Plants", in: *Methods in Plant Molecular Biology and Biotechnology*, Glick and Thompson, eds., CRC Press, Inc., Boca Raton, pages 67–88 (1993). The methods chosen vary with the host plant, and include chemical transfection methods such as calcium phosphate, microorganism-mediated gene transfer such as Agrobacterium (Horsch et al., *Science*, 227:1229–31 (1985)), electroporation, micro-injection, and biolistic bombardment.

Expression cassettes and vectors and in vitro culture methods for plant cell or tissue transformation and regeneration of plants are also known and available. See, for example, Gruber et al., "Vectors for Plant Transformation," in: *Methods in Plant Molecular Biology and Biotechnology*, Glick and Thompson, eds., CRC Press, Inc., Boca Raton, pages 89–119 (1993). As used herein, an "expression cassette" is a nucleic acid construct, generated recombinantly or synthetically, with a series of specified nucleic acid elements which permit transcription of a particular nucleic acid in a host cell. The expression cassette can be incorporated into a plasmid, chromosome, mitochondrial DNA, plastid DNA, virus, or nucleic acid fragment. Typically, the expression cassette portion of an expression vector includes, among other sequences, a nucleic acid to be transcribed, and a promoter.

Agrobacterium-mediated Gene Delivery

One widely utilized method for introducing an expression vector into plants is based on the natural transformation system of Agrobacterium. *A. tumefaciens* and *A. rhizogenes* are plant pathogenic soil bacteria that genetically transform plant cells. The Ti and Ri plasmids of *A. tumefaciens* and *A. rhizogenes*, respectfully, carry genes responsible for genetic transformation of plants (see, e.g., Kado, *Crit. Rev.Plant Sci.*, 10: 1 (1991)). Descriptions of the Agrobacterium vector systems and methods for Agrobacterium-mediated gene transfer are provided in Gruber et al., supra, see also Hiei, et al., U.S. Pat. No. 5,591,616, issued Jan. 7, 1997.

Direct Gene Transfer

Despite the fact that the host range for Agrobacterium-mediated transformation is broad, some major cereal crop species and gymnosperms have generally been recalcitrant to this mode of gene delivery, even though some success has recently been achieved in rice and maize (Hiei et al., *The Plant Journal*, 6:271–282 (1994); Ishida et al., *Nature Biotechnology*, 14:745–750 (1996), Hiei, et al., U.S. Pat. No. 5,591,616, issued Jan. 7, 1997). Several other methods of introducing foreign DNA into plant cells, collectively referred to as direct gene transfer, have been developed as an alternative to Agrobacterium-mediated delivery.

A generally applicable method of delivering DNA into plant cells is microprojectile-mediated delivery, where DNA is carried on the surface of microprojectiles measuring about 1 to 4 $\mu$M in diameter. The expression vector is introduced into plant tissues with a biolistic device that accelerates the microprojectiles to speeds of 300 to 600 m/s which is sufficient to penetrate the plant cell walls and membranes. (e.g., Klein et al., *Biotechnology*, 10:268 (1992)).

Another method for physical delivery of DNA to plants is sonication of target cells as described in Zang et al., *Bio/Technology*, 9:996 (1991). Alternatively, liposome or spheroplast fusions have been used to introduce expression vectors into plants (see, e.g., Christou et al., *Proc. Nat'l Acad. Sci. (U.S.A.)*, 84:3962 (1987)). Direct uptake of DNA into protoplasts using $CaCl_2$ precipitation, polyvinyl alcohol or poly-L-ornithine have also been reported. (See, for example, Hain et al., *Mol. Gen. Genet.*, 199:161 (1985)). Electroporation of protoplasts and whole cells and tissues has also been described (see, for example, Spencer et al., *Plant Mol.Biol.*, 24:51–61 (1994)).

Particle Wounding/Agrobacterium Delivery

Another useful basic transformation protocol involves a combination of wounding by particle bombardment, followed by use of Agrobacterium for DNA delivery, as described by Bidney et al., *Plant Mol. Biol.*, 18:301–313 (1992). Useful plasmids for this delivery method are ones containing a Bin 19 backbone (see Bevan, *Nucleic Acids Research*, 12:8711–8721 (1984)). This method is commonly used to deliver heterologous DNA into sunflower cells.

Assay Methods

Transgenic plant cells, callus, tissues, shoots, and transgenic plants may be tested for a presence of the ZmRAD51 gene by DNA analysis and for expression of the gene by immunoassay. For example, the presence of a ZmRAD51 gene can be confirmed by Southern analysis. This common procedure may be carried out by isolating DNA from the cells in question, cutting the DNA using restriction enzymes, fractionating the resulting DNA fragments on an agarose gel to separate the fragments by molecular weight. The separated DNA fragments are then transferred to nitro-cellulose membranes and hybridized with a radioactively labeled probe fragment (e.g., labeled with $^{32}P$) and washed with an SDS solution (see, e.g., Southern, *J. Molec. Biol.*, 98:503–517 (1975)). Alternatively, the presence of the ZmRAD51 gene in transgenic cells may be verified by amplifying the gene (or a portion of the gene) by polymerase chain reaction ("PCR") using appropriate primers, cutting the DNA from the PCR with restriction enzymes, and fractionating the resulting DNA fragments as described above and detecting the PCR amplified DNA fragment with an appropriate probe (see, e.g., Saiki, *Science*, 239:487–491 (1988)).

Instead of examining the transgenic cells for the presence of the ZmRAD51 gene, expression of the gene by the transgenic cell may be probed using an immunoassay technique to establish the presence of expressed ZmRAD51 protein. This is typically carried out by probing the protein fraction from the transgenic cells with an antibody specific for the ZmRAD51 protein. The presence of the resulting ZmRAD51 protein/antibody complex can be detected using a variety of well known techniques.

The invention is further characterized by the following examples. These examples are not meant to limit the scope of the invention as set forth in the foregoing description and variations within the concepts of the invention will be apparent.

EXAMPLES

Example 1

Cloning of ZmRAD51A & ZmRAD51B cDNA

A. Recovery of a ZmRAD51 Probe Fragment

Poly-A mRNA from maize (cv. A632) tassels was prepared using the MicroQuick kit (Pharmacia, Piscataway, N.J.). Room temperature PCR was performed on the mRNA using a set of degenerate primers designed from known-RAD51 consensus sequences. The PCR amplified fragment was cloned and sequenced, and confirmed to be a 360 bp cDNA sequence for a RAD51 homolog. The probe fragment clone corresponding to the *Zea mays* cDNA was designated PHP7763 and had the following sequence:
ACATTCAGACCACAAAGGCTCTTGCA-GATTGCTGACAGGTTTGGACTGAATGGT-GCTGATGTGTTAGAGAATGTGGCTTAT-GCCAGAGCTTATAATACGGATCATCAATCTAGA CTTCTGCTGGAAGCAGCTTCCATGAT-GATAGAGACCAGGTTTACTCTTATGGT-TGTAGACAGTGCCACAGCTCTGTACA-GAACTGATTTCTCAGGAAGAGGGGAACTATC AGCGAGGCAAATGCACATGGCTAAGTTC-CTGAGGAGCCTTCAGAAGTTAGCTGAT-GAGTTTGGAGTAGCTGTGGTTATCAC-CAATCAAGTAGTGGCCCAAGTGGATGGATCTAC TATGTTTGCTGGGCCGCAGTTC (SEQ ID NO: 11).

The PHP7763 probe sequence was used to design and synthesize two maize sequence-specific oligonucleotide primers, PHN7443 having the nucleotide sequence 5'-TATAGAATTCCACAAAGGCTCTTGCAGATTGC TGACAG (SEQ ID NO: 12) and PHN7444 having the sequence,
5'-ATACTCGAGGCCCAGCAAACATAGTAGATCC ATCCAC (SEQ ID NO:13).

B. Lambda Library Screening

A lambda cDNA library made by Stratagene (LaJolla, Calif.) from supplied maize (cv. A632) tassel RNA was screened using standard procedures as described in *Molecular Cloning: A Laboratory Manual*, Second Edition, Sambrook, Fritsch and Maniatis, Cold Spring Harbor Laboratory Press, (1989). The library was plated at approximately 50,000 plaques per 150 mm plate, transferred to filters (Magnalift brand, MSI, Inc. Westborough, Mass.), and screened using a digoxigenin-dUTP-labeled PCR amplified probe generated using oligonucleotide primers PHN7443 and PHN7444. Labeling and hybridization conditions were as described in the Genius™ System manual by the manufacturer (Boerhinger Mannheim Corp., Indianapolis, Ind.), with modifications. The full protocols used are listed in Examples 3 and 4.

The filter probing resulted in 32 spots which aligned well on the lumigraphs from duplicate lifts, 11 more with less optimal alignment, 8 with fair aligmnent and 23 with no corresponding alignment on the duplicate lift. The corresponding plaques were picked for further evaluation. Additional PCR amplification reactions designed to eliminate false positives were carried out using the PHN7443 and PHN7444 primers above plus M13 forward (PHN162, 5'-TCCCAGTCACGACGTTGTAAAACG SEQ ID NO: 14); and reverse (PHN487, 5'-AGCGGATAACAATTTCACACAGGAAACAGCTA TGAC SEQ ID NO: 15) primers. Six plaque picks were recovered, titered, replated to give several hundred plaques per plate and lifted and reprobed as described above. Confirmed positive plaques were processed through an in vivo "pop-out" protocol that generates phagemid (plasmid) DNA from infecting lambda phage. The protocol used was developed at Stratagene (La Jolla, Calif.) and is described in the directions that accompany their Lamda Zap libraries. When successfully performed, this procedure yields *E. coli* colonies that contain a pBlueScript™ (Stratagene, La Jolla, Calif.) type plasmid that has been excised from the lambda phage. Each plaque pick used yielded several colonies following this protocol. Additional screening of the plasmid clones resulted in three unique clones, as determined by restriction enzyme analysis. Partial sequencing and comparison to known higher eukaryotic RAD51 genes confirmed that these clones corresponded to maize homologs of RAD51. Of the three clones, two were identical in sequence except that one of the two had a longer 3' untranslated region and was truncated in the coding region. The third clone shared very high identity in the coding region with the first two clones, but differed in the untranslated regions. The three clones were designated PHP7981, PHP7982 and PHP7983. PHP7981 (ZmRAD51A) and PHP7983 (ZmRAD51B) were completely sequenced (see Tables I and II herein). The RAD51A 3' untranslated region can be seen in SEQ ID NO:4 (nucleotide 1078 to 1538) and the RAD51B 3' untranslated region can be seen in SEQ ID NO:8 (nucleotide 1099 to 1556).

In order to facilitate later cloning of the ZmRAD51 genes, site-directed mutagenesis (by the method of Su et al., *Gene*, 69:81–89 (1988)) was used to introduce restriction sites flanking the coding sequences. A HpaI restriction site was introduced downstream of the stop codon of PHP7981 (position shown in Table I) using the oligonucleotide primer PHN9611 (5'-GTATTGCAGATGTTAAGGATTGAGACCATACCT GGTTAACAGGCATCTCAG3'-SEQ ID NO: 16) to create the plasmid PHP8057. A BamHI site was introduced 5' to the start codon of PHP7983 (position shown in Table II) with the primer PHN9612 (5'-GCAGCCAGGGATCCAC-ATGTCCTCGTC3'-SEQ ID NO: 17), and a HpaI site was inserted 3' to the stop codon (position shown in Table II) with oligonucleotide PHN9613 (5'-CTGATGTCAAGGACTGAAAGCATCCTCATTTG CAGTTAACAGCATAACTTGC3'-SEQ ID NO:18) to create the plasmid PHP8058. These newly created clones served as sources of probes for mapping studies.

Example 2

Mapping of the Maize ZmRAD51 Clones

For ZmRAD51 sequence-specific hybridization, oligonucleotide primers homologous to unique sequences in the 3' untranslated regions of ZmRAD51A (PHN10664; 5'-CCATACCTGCTTTACAGGCATC3'-SEQ ID NO:19) or of ZmRAD51B (PHN10665; 5'-CATCCTCATTTGSAGTCCACAG3'-SEQ ID NO:20; where "S" denotes a mixture of "C" and "G") were synthesized and used in conjunction with an M13 universal sequencing primer (PHN162; 5'-TCCCAGTCACGACGTTGTAAAACG3' SEQ ID NO: 14) to PCR amplify probe fragments from the two vectors PHP8057 (ZmRAD51A) and PHP8058 (ZmRAD51B). Sequences of PHN10664 and PHN10665 span the regions mutagenized to create the HpaI sites, but themselves correspond to the sequences of the original clones in PHP7981 and PHP7983. There was enough identity to permit efficient PCR amplification using PHP8057 and PHP8058 as templates. This approach was used in order to generate final probe fragments identical to the original ZmRAD51A and ZmRAD51B genes. These fragments, which extend from just downstream of the translation stop codon to the end of the poly(A) tail of the cDNA sequences, were subsequently used as probes against two maize populations and map positions were determined.

Southern hybridizations were carried out using two different maize populations generated as part of a breeding program. Population 1 (MARSA), an F4, was generated from crosses of the lines R03×N46, and included 200 individuals as part of the mapping family. Population 2 (ALEB9), an F2, was generated from crosses of the lines R67×P38 and contained 240 individuals. DNA was isolated from each individual by a CTAB extraction method (Saghai-Maroof et al., *Proc. Nat'l Acad. Sci.* (U.S.A.), 81:8014–8018 (1994)) and digested individually with restriction enzymes BamHI, HindIII, EcoRI and EcoRV. Digests were separated on agarose gels and transferred to membranes (Southern, *J. Molec. Biol.*, 98:503–517 (1975)) prior to hybridization (Helentjaris et al., *Plant Mol. Biol.*, 5:109–118 (1985)) with an array of probes to establish the basic RFLP map. Population 1 membranes were hybridized using 179 RFLP probes, while population 2 membranes were hybridized using 115 RFLP probes. After hybridization the membranes were exposed to x-ray film for an appropriate length of time to be visually scored. All data were entered into an electronic database and map positions of the RFLP probes (Evola et al., *Theor. Appl. Genet.*, 71:765–771(1986)) were determined using MAPMAKER (Lincoln et al., in *Constructing Genetic Linkage Maps with MAPMARKER/EXP Version 3.0: A Tutorial and Reference Manual*, Whitehead Institute for Biomedical Research, Cambridge, Mass. (1993)) and a map was constructed for each population. Table VI lists the positions of a number of markers, including the ZmRAD51A gene, mapped on the MARSA population. Table VII lists the positions of a number of markers, including the ZmRAD51B gene, mapped on the ALEB9 population.

Example 3

Hybridization Procedure

A prehybridization solution was prepared containing the following components:
 1% BMB Blocking reagent
 1% gelatin
 0.2% SDS
 0.1% Sarkosyl (n-lauryl sarkosine)
 5×SSC (750 mM sodium chloride, 75 mM sodium citrate, pH 7.0)

The solution was heated to facilitate the dissolution of the blocking reagent and the gelatin. After being wet with 2×SSC, filters were placed in the prehybridization solution and incubated at 68° C. for 2 hrs with shaking.

Hybridization was carried out by a procedure which included denaturing a Digoxigenin labeled probe by boiling for 10 minutes and then plunging into an ice water bath. The probe was added to give 10 to 20 ng of probe per ml of prehybridization solution and mixed well to form a hybridization solution. If the hybridization solution was to be reused, it was heated to 95° C. for 10 minutes. The equilibrated filters were incubated overnight at 68° C., with gentle shaking or other form of agitation.

The incubated filters were washed for 5 minutes in a dish with 2×SSC+0.1% SDS. This wash was repeated two additional times. The filters were then washed two times for 1.5 hrs in 0.5×SSC+0.1% SDS at 60–65 C. using pre-warmed wash solution.

Example 4

Labeling Procedure

A. Antibody Probing

Antibody probing was conducted by performing the following steps with individual filters in Petri dishes. A Genius™ blocking solution was prepared by dissolving 1% BMB Block, 1% Gelatin and 0.5% Tween 20 in Genius™ 1 buffer. The Genius™ 1 buffer was heated to dissolve the blocking reagent and gelatin, then cooled to room temperature.

Filters were washed 3 times in Genius™ 1 Buffer (5 minutes per wash) and then incubated 1 hr in Genius™ Blocking solution, with gentle rocking. An anti-digoxigenin/alkaline phosphate conjugate was diluted 1:100 in leftover block (directly into the blocking solution on the filters). After incubation for 0.5 hour, the filters were washed 2 times for 15 minutes in Genius™ 1 Buffer.

B. Chemiluminescent Read-out

Without being allowed to dry, filters were washed 2 times in Genius™ Buffer 3 (15 minutes per wash). At the start of the first wash, LumiPhos530 was taken out of the refrigerator. X-Ray cassettes were prepared by placing transparency sheets (3M AF4300 sheets) in the cassettes and taping them in place. About 6 mL of LumiPhos530 was placed into a Petri dish lid, taking care to handle the LumiPhos aseptically. Filters were removed from the Genius™ Buffer 3 and most of the buffer was wicked onto Whatman 3 mm paper by just touching the filter's edge to the Whatman paper. The filter was then placed plaque side down onto the LumiPhos530, ensuring good coverage on the plaque side and allowing most of the LumiPhos to drain off back into the lid. The filter was then placed in the X-ray cassette, plaque side up, on the transparency sheet(s). As soon as a transparency sheet was full, another sheet was placed on top of it and bubbles were smoothed out. The top sheet was taped in place. Putting the top sheet in place quickly prevented the filters from drying out. The filters in the transparency sheet were exposed to a Kodak XAR-5 film sheet for 1 to 1.5 hrs. This first film was developed and another XAR-5 sheet was exposed overnight. The overnight sheet was very overexposed, but the stab marks showed as white spots, allowing ready alignment of the plate to the lumigraph.

Figure 3:
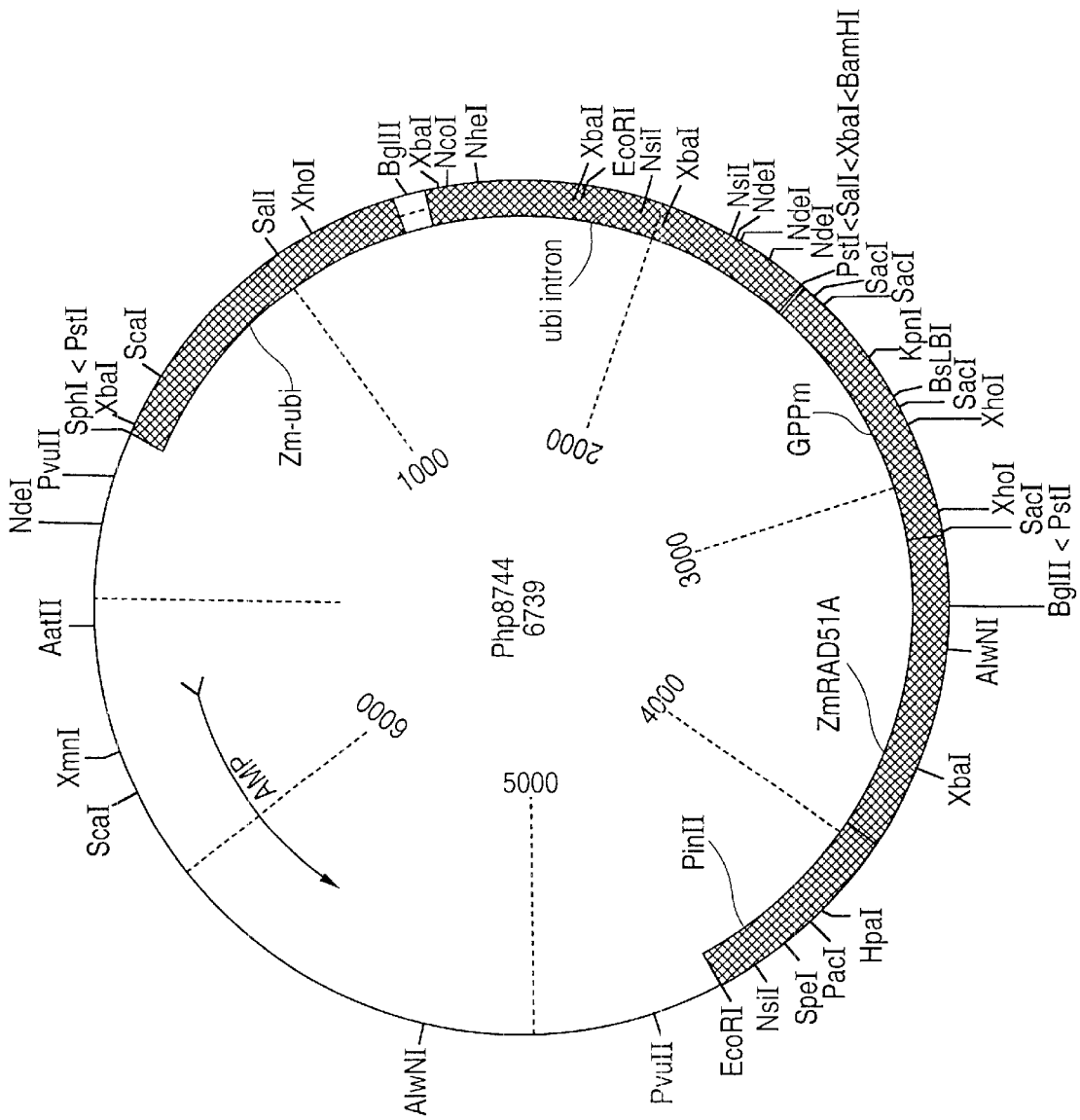
FIG. 3 shows a map of a plasmid designated PHP8744 derived from the insertion of a GFPm gene 5' to the start of the modified ZmRAD51A gene in PHP8060 to create a sequence encoding a GFP/ZmRAD51A fusion protein. Optionally, the modified ZmRAD51B gene could be placed instead of the modified ZmRAD51A gene, to form a GFP/ZmRAD51B fusion gene.

To construct the protein fusions, the GFPm stop codon was removed and a BglII site was generated by site-directed mutagenesis. This 0.8 kb BamHI/BglII fragment of the GFPm coding sequence was inserted into the BamHI site 5' to the start of ZmRAD51 in PHP8060 and PHP8103 from above to create PHP8744 (FIG. 3) and PHP8745, respectively. This process created fusions of GFPm to ZmRAD51A or ZmRAD51B joined by a 6 bp linker encoding isoleucine and histidine (junctions shown below).

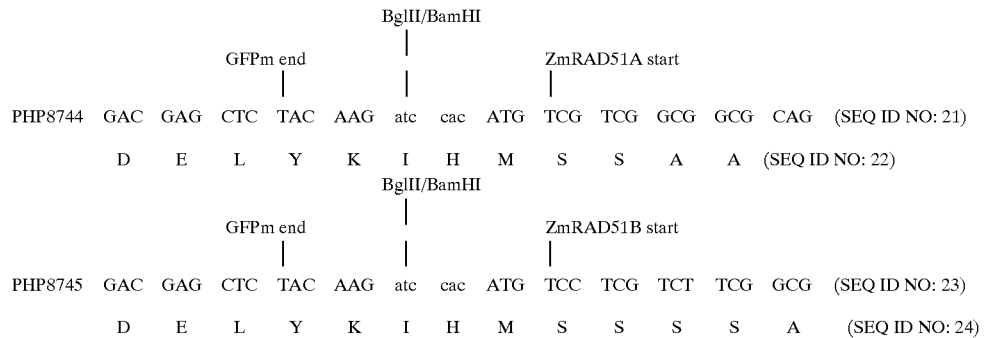

C. Picking Plaques

Tubes were prepared with SM buffer (100 mM NaCl, 8 mM MgSO$_4$-7H$_2$O, 50 mM Tris-Cl, pH 7.5, 0.01% (w/v) gelatin), usually about 1 mL. Stab marks on the plates were aligned to the marks on the lumigraph. Plaques of interest were picked by poking a pipette into the agar and remove a plug containing the plaque using either the back of a 5 mL pipette (for 1° picks) or a transfer pipette (for 2° picks). Each plug was added to a tube containing the SM buffer. One drop of chloroform (free of isoamyl alcohol) was then added to the buffer. After capping and vortexing well, the tube was then incubated at room temperature for 1 to 2 hours, and then stored at 4° C.

Example 5

Creation of ZmRAD51—Containing Plant Transformation Vectors

Figure 2:
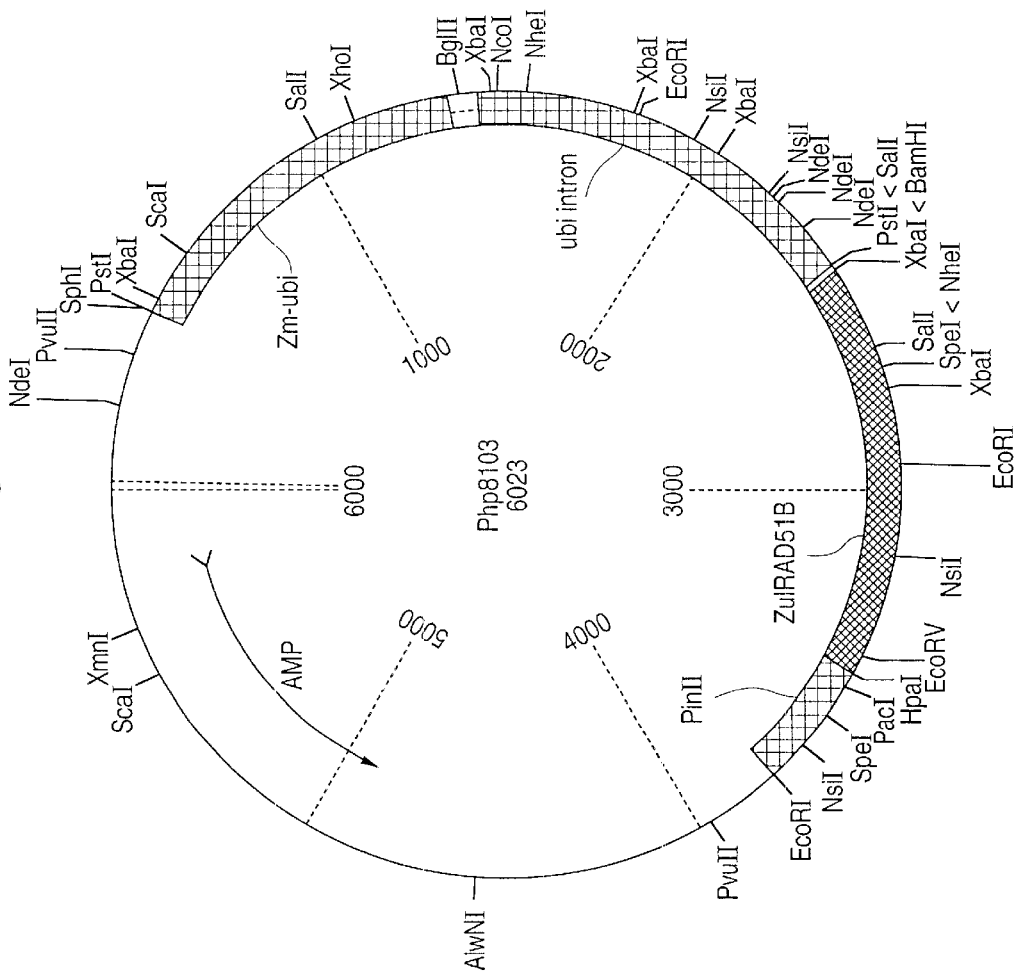
FIG. 2 shows a map of a plasmid designated PHP8103 derived from the insertion of a modified ZmRAD51B gene between a maize ubiquitin promoter and a potato proteinase inhibitor ("PinII") terminator in a pUC19 plasmid backbone.

Constructs for plant transformation experiments were created in which the ZmRAD51A or ZmRAD51B genes were inserted behind a maize ubiquitin promoter (Christensen et al., *Plant Mol. Biol*, 18:1185–1187 (1992)). To facilitate cloning the two ZmRAD51 genes as BamHI/HpaI fragments, a BamHI site was created 5' to the start of translation of ZmRAD51 in PHP8057 by PCR. The PCR-modified ZmRAD51A and the ZmRAD51B genes from PHP8057 and PHP8058 then were inserted as BamHI/HpaI fragments downstream of the 2.0 kb PstI fragment of the maize ubiquitin promoter and upstream of the potato proteinase inhibitor II (PinII) terminator (bases 2 to 310 from An et al., *Plant Cell*, 1:115–122 (1989)) in a pUC19 plasmid backbone to make PHP8060 (FIG. 1) and PHP8103 (FIG. 2).

Another set of constructs was made using either the ubiquitin promoter or the maize ZmDJ1 promoter (Baszczynski et al., *Maydica*, 42:189–201 (1997)), but where the complete ZmRAD51A or ZmRAD51B genes were first fused to the 3' end of a green fluorescence protein ("GFP"; Chalfie et al., *Science*, 263:802–805 (1994)) gene that was previously synthesized so as to encode maize-preferred codons (new gene designated "GFPm") as described in PCT Patent Application No. PCT/US97/07688.

To create versions of these constructs utilizing the maize ZmdJ1 promoter, the 1.8 kb BamHI/HpaI fragments containing GFPm/ZmRAD51A and GFPm/ZmRAD51B coding sequences from PHP8744 and PHP8745 were inserted downstream of the 0.8 kb SacI/BglII ZmDJ1 promoter sequence and upstream of the PinII terminator in a pBlueScript™ plasmid backbone to generate PHP8961 and PHP8962.

Example 6

Introduction of ZmRAD51 Gene Constructs into Maize Cells and Detection of Gene Expression The various constructs described in Example 5 were introduced into cells of the Black Mexican Sweet ("BMS") maize line (Sheridan, *J. Cell Biol.*, 67:396a (1975)) by particle gun bombardment using 1 ug of plasmid per particle preparation at 6 shots per preparation. About 100 mg of BMS cells per plate were shot. For experiments utilizing PHP8060 or PHP8103, another construct, PHP9053, which carried a fusion between a nuclear localization sequence (NLS), the GFPm gene as above and a maize acetolactate synthase (ALS) gene (Fang et al., *Plant Mol. Biol.*, 18:1185–1187 (1992)), all driven from the ubiquitin promoter was shot concurrently. To create PHP9053, the nuclear localization signal from simian virus 40 (SV40) (Kalderon et al., *Cell*, 39:499–509 (1984)) was synthesized as a BamHI/NcoI fragment and inserted at BamHI and AflIII sites between the ubiquitin promoter and the start codon of GFPm. In order to enhance retention of the protein in the nucleus, the molecular weight of NLS/GFPm and hence the size of the protein was increased by making a carboxy terminal fusion with a large unrelated protein, in this case the maize ALS gene. The ALS coding sequence was inserted in frame at the GFPm 3' BglII site and blunt-end ligated to the PinII terminator. Cells were viewed at 24–48 hours post-bombardment for GFP expression using a microscope equipped with epi-fluorescence and a FITC filter set.

In all cases, GFP expression was noted in the nucleus. At no time was GFP fluorescence noted in the cytoplasm, either when GFP was part of a fusion that included the NLS, or as a fusion only with ZmRAD51A or ZmRAD51B. The data obtained with PHP8744, PHP8745, PHP8961 and PHP8962 indicate that the expressed RAD51A or RAD51B proteins (in this case as fusions with GFP) localize to the nucleus in the absence of an exogenously added sequence known to facilitate nuclear localization (i.e., the SV40 NLS sequence). Comparable localization results were obtained using two independent promoters (maize ubiquitin or the ZmDJ1 promoters) indicating the information for nuclear localization is located within the ZmRAD51 coding sequences. With constructs containing GFP alone, expression does not localize to the nucleus. The ZmRAD51 nuclear localization sequence is located within in the 5' end of the coding region, preferably the first 40 amino acids of sequence SEQ ID NO: 3 or 7, more preferably the first 30 amino acids of SEQ ID NO: 3 or 7, even more preferably the first 20 amino acids of SEQ ID NO: 3 or 7 or most preferably the first 10 amino acids. The corresponding polynucleotide sequence would be from nucleotide 53 to 113 of SEQ ID NO: 1 or nucleotide 73 to 132 of SEQ ID NO:5 and fragments thereof.

As such, the methods and constructs disclosed provide a means of introducing maize RAD51 genes, or fusions of other genes with the maize RAD51 genes into maize cells and maize nuclei, stably expressing the gene products under constitutive or inducible control and studying the role of these genes in plant cells.

Example 7

Expression of ZmRAD51 Genes in an *E. coli* Host Cell

*E. coli* expression vectors PHP9011 and PHP9012 were constructed by insertion of BamHI/HpaI fragments containing the ZmRAD51A and ZmRAD51B genes from PHP8057 and PHP8058, respectively, into the BamHI and HindII sites in a pET32c plasmid (Novagen, Inc., Madison, Wis.). The resulting plasmids consisted of the T7 promoter driving expression of a protein containing a 108 amino acid thioredoxin tag, a 6 amino acid histidine tag, a thrombin cleavage site, a 15 amino acid S tag (Novagen Inc., Madison, Wis.), and an enterokinase cleavage site fused to the amino terminus of one of the full length ZmRAD51 coding sequences.

The two constructs PHP9011 and PHP9012 were each transformed into the Novagen pET *E. coli* host strain AD494 (DE3)pLysS, and used subsequently to express and purify ZmRAD51 A and ZmRAD51 B protein, respectively, according to the following procedure.

*E. coli* cells transformed with either the PHP9011 or the PHP9012 expression vector were incubated in 2YT media (Life Technologies, Gaithersburg, Md.) containing, 100 ug/ml carbenicillin, and 34 ug/ml chloramphenicol. Cells were induced at approximately OD600=0.8 with 0.2 mM IPTG (isopropyl-1-thio-β-D-galactoside) and incubated at room temperature for 3 hours.

The cells were then lysed in a lysis buffer containing 50 mM Tris-HCl (pH 8.0), 500 mM NaCl, 5 mM 2-mercaptoethanol, 1 mM PMSF (phenylmethylsulfonylfluoride), 0.1% Triton X-100, 10% Glycerol and 5 mM imidazole.

Purification of the cell lysate was carried out at 4° C. on a TALON metal affinity column equilibrated with a solution containing 50 mM Tris-HCl pH 8.0, 500 mM NaCl, 0.1% Triton X-100, 10% Glycerol and 5 mM imidazole ("equilibrium buffer"). Lysate was loaded onto the equilibrated TALON column. The loaded column was washed with the equilibrium buffer and then washed with a solution of 50 mM Tris-HCl (pH 8.0), 10% Glycerol and 5mM imidazole. The washed column was then eluted with a solution containing 50 mM Tris-HCl (pH 8.0), 10% Glycerol and 100 mM Imidazole. 1 mM DTT and 1 mM EDTA were added to eluted protein, which was then stored at 4° C. The expressed fusion proteins were processed and purified as follows. The expressed fusion proteins were first dialyzed to remove imidazole and the dialyzed fusion proteins were site-specifically cleaved with enterokinase to remove the thioredoxin tag. The cleavage products were purified on the Talon column to remove the cleaved tag fragment. Yields of protein were 3 mg/L for ZmRAD51A and 1.5 mg/L for ZmRAD51B.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

TABLE I

FULL LENGTH cDNA AND
CORRESPONDING AMINO ACID SEQUENCE FOR ZmRAD51A

```
LOCUS       ZMRAD51A (Sequence corresponding to cDNA insert in PHP7981)
FEATURES    peptide from 53 to 1072
ORIGIN      Zea mays A632 line 1     GGCACGAGTTCGAACAGGGGCAGAGGTGAGACTTGAGAGAAGGAAGAAGGTCATGTCGTC
                                                                  M  S  S 61     GGCGGCGCAGCAGCAGCAGAAAGCGGCGGCAGCGGAGCAGGAGGAGGTGGAGCACGGGCC
            A  A  Q  Q  Q  Q  K  A  A  A  A  E  Q  E  E  V  E  H  G  P 121     ATTCCCCATCGAGCAGCTCCAGGCTTCTGGAATAGCTGCATTGGATGTGAAGAAGCTGAA
            F  P  I  E  Q  L  Q  A  S  G  I  A  A  L  D  V  K  K  L  K 181     AGATTCTGGTCTCCACACTGTGGAGGCTGTGGCTTACACTCCAAGGAAAGATCTTCTGCA
            D  S  G  L  H  T  V  E  A  V  A  Y  T  P  R  K  D  L  L  Q 241     GATCAAAGGGATAAGTGAAGCTAAAGCTGACAAGATAATTGAAGCAGCATCCAAGATAGT
            I  K  G  I  S  E  A  K  A  D  K  I  I  E  A  A  S  K  I  V
```

TABLE I-continued

FULL LENGTH cDNA AND CORRESPONDING AMINO ACID SEQUENCE FOR ZmRAD51A

```
LOCUS     ZMRAD51A (Sequence corresponding to cDNA insert in PHP7981)
FEATURES  peptide from 53 to 1072
ORIGIN    Zea mays A632 line
```

```
 301   TCCACTGGGATTTACAAGTGCCAGTCAACTTCATGCGCAGCGACTGGAGATTATTCAAGT
         P  L  G  F  T  S  A  S  Q  L  H  A  Q  R  L  E  I  I  Q  V

361   TACAACTGGATCAAGAGAGCTTGATAAGATATTGGAGGGTGGGATAGAAACAGGATCTAT
         T  T  G  S  R  E  L  D  K  I  L  E  G  G  I  E  T  G  S  I

421   CACTGAGATATATGGTGAGTTCCGCTCTGGAAAGACTCAGTTGTGTCACACCCCTTGTGT
         T  E  I  Y  G  E  F  R  S  G  K  T  Q  L  C  H  T  P  C  V

481   TACATGTCAGCTTCCACTGGACCAGGGTGGTGGTGAAGGAAAGGCTCTATATATTGACGC
         T  C  Q  L  P  L  D  Q  G  G  G  E  G  K  A  L  Y  I  D  A

541   AGAGGGTACATTCAGACCACAAAGGCTCTTGCAGATTGCTGACAGGTTTGGACTGAATGG
         E  G  T  F  R  P  Q  R  L  L  Q  I  A  D  R  F  G  L  N  G

601   TGCTGATGTGTTAGAGAATGTGGCTTATGCCAGAGCTTATAATACGGATCATCAATCTAG
         A  D  V  L  E  N  V  A  Y  A  R  A  Y  N  T  D  H  Q  S  R

661   ACTTCTGCTGGAAGCAGCTTCCATGATGATAGAGACCAGGTTTGCTCTTATGGTTGTAGA
         L  L  L  E  A  A  S  M  M  I  E  T  R  F  A  L  M  V  V  D

721   CAGTGCCACAGCTCTGTACAGAACTGATTTCTCAGGAAGAGGGGAACTATCAGCGAGGCA
         S  A  T  A  L  Y  R  T  D  F  S  G  R  G  E  L  S  A  R  Q

781   AATGCACATGGCTAAGTTCCTGAGGAGCCTTCAGAAGTTAGCTGATGAGTTTGGAGTAGC
         M  H  M  A  K  F  L  R  S  L  Q  K  L  A  D  E  F  G  V  A

841   TGTGGTTATCACCAATCAAGTAGTGGCCCAAGTGGATGGATCTGCTATGTTTGCTGGACC
         V  V  I  T  N  Q  V  V  A  Q  V  D  G  S  A  M  F  A  G  P

901   GCAGTTCAAGCCCATTGGTGGAAACATCATGGCTCATGCTTCAACCACAAGGCTTGCTCT
         Q  F  K  P  I  G  G  N  I  M  A  H  A  S  T  T  R  L  A  L

961   TCGCAAGGGGCGAGGGGAGGAACGGATCTGTAAAGTAATAAGCTCTCCCTGCCTTGCTGA
         R  K  G  R  G  E  E  R  I  C  K  V  I  S  S  P  C  L  A  E

1021   AGCCGAAGCAAGGTTTCAGTTAGCTTCTGAAGGTATTGCAGATGTTAAGGATTGAGACCA
         A  E  A  R  F  Q  L  A  S  E  G  I  A  D  V  K  D

1081   TACCTGCTTTACAGGCATCTTCAGATCCATTGGTCTGCTATTTGCTTTGTCATTCCTTGG
              G.TTAAC (HpaI)

1141   GCCAACTTTCGTGTTGCCTCACCTTGATGTACAAAACGGTTTCGTTCACATATGTGAATG

1201   CACGCCTGTGACTGATTTAGGCGTCCTGTTGTAAATAAAACGATGCCTGTTGCCCTGTTG

1261   TGTGTTGCATGTAATCGACAACTCTACATATCACAATTATGATGTATTTTAGGTTTTATT

1321   GTTCGCTTAGCACAGCCATTGCTGGATGTGCAATGTGGGATTATAGACAAGAATCCACAC

1381   AACAACAATGGCCAATCCTGATAAAGTAGTTAGTGACTTGGGCAAATAGCATTGTGGTGA

1441   TCTTTGAGTTCACTTGTGATAAGAACAGGGCTGGTGGCTGGTGGTGAAAACTAACTTGTG

1501   ATCGGAACAGGTTTAATAGGGAAAACTAAGGATTCTATAAAAAAAAAAATAAAAAAAAAA

1561   AAAAAAAA
```

TABLE II

FULL LENGTH cDNA AND CORRESPONDING AMINO ACID SEQUENCE FOR ZmRAD51B

LOCUS    ZmRAD51B (Sequence corresponding to cDNA insert in PHP7983)
FEATURES  peptide from 53 to 1072
ORIGIN    *Zea mays* A632 line

```
   1 GAATTCGGCACGAGATTTTTTGCCGCTTCGGAGGCACCTTCGAACAAAGCCCAAAAGCAG

61 CCAGCGCACCGCATGTCCTCGTCTTCGGCGCACCAGAAGGCGTCGCCGCCGATAGAGGAG
                  M   S   S   S   S   A   H   Q   K   A   S   P   P   I   E   E
       GGATCC (BamHI)

121 GAAGCGACGGAGCACGGACCCTTCCCCATCGAACAGCTACAGGCATCTGGAATAGCTGCA
      E   A   T   E   H   G   P   F   P   I   E   Q   L   Q   A   S   G   I   A   A

181 CTTGATGTGAAAAAACTCAAAGATGCTGGTCTCTGCACAGTGGAATCTGTAGCATACTCT
      L   D   V   K   K   L   K   D   A   G   L   C   T   V   E   S   V   A   Y   S

241 CCAAGGAAAGACCTTTTGCAAATTAAAGGGATTAGTGAAGCCAAAGTCGACAAGATAATT
      P   R   K   D   L   L   Q   I   K   G   I   S   E   A   K   V   D   K   I   I

301 GAAGCAGCTTCCAAGTTGGTTCCACTCGGATTTACTAGTGCTAGCCAACTTCATGCACAG
      E   A   A   S   K   L   V   P   L   G   F   T   S   A   S   Q   L   H   A   Q

361 AGACTTGAGATCATCCAGCTTACAACTGGATCTAGAGAGCTTGATCAAATTTTGGACGGT
      R   L   E   I   I   Q   L   T   T   G   S   R   E   L   D   Q   I   L   D   G

421 GGAATAGAAACAGGATCTATCACAGAGATGTATGGTGAATTTCGCTCCGGAAGACTCAG
      G   I   E   T   G   S   I   T   E   M   Y   G   E   F   R   S   G   K   T   Q

481 TTGTGCCACACTCTCTGTGTCACATGTCAGCTCCCATTGGACCAAGGTGGTGGTGAAGGA
      L   C   H   T   L   C   V   T   C   Q   L   P   L   D   Q   G   G   G   E   G

541 AAGGCTTTGTATATTGATGCAGAGGGTACATTCAGGCCTCAAAGAATTCTCCAGATAGCA
      K   A   L   Y   I   D   A   E   G   T   F   R   P   Q   R   I   L   Q   I   A

601 GACAGGTTTGGCTTGAATGGCGCTGATGTACTAGAGAATGTGGCTTATGCCAGAGCATAT
      D   R   F   G   L   N   G   A   D   V   L   E   N   V   A   Y   A   R   A   Y

661 AACACTGATCATCAATCAAGACTTTTGCTAGAAGCAGCCTCCATGATGGTAGAGACCAGG
      N   T   D   H   Q   S   R   L   L   E   A   A   S   M   M   V   E   T   R

721 TTTGCTCTCATGGTTGTGGATAGTGCTACAGCCCTTTACAGAACTGATTTCTCTGGTAGA
      F   A   L   M   V   V   D   S   A   T   A   L   Y   R   T   D   F   S   G   R

781 GGGGAGCTATCAGCAAGGCAGATGCATCTGGCGAAGTTTCTTAGGAGCCTTCAAAAGTTA
      G   E   L   S   A   R   Q   M   H   L   A   K   F   L   R   S   L   Q   K   L

841 GCAGATGAGTTTGGAGTGGCAGTGGTAATCACGAACCAAGTAGTGGCTCAAGTGGATGGT
      A   D   E   F   G   V   A   V   V   I   T   N   Q   V   V   A   Q   V   D   G

901 GCTGCAATGTTTGCTGGGCCACAGATCAAGCCCATTGGAGGGAACATCATGGCTCATGCT
      A   A   M   F   A   G   P   Q   I   K   P   I   G   G   N   I   M   A   H   A

961 TCCACAACTAGGCTCTTTCTTCGCAAGGGAAGAGGGGAGGAGCGGATCTGCAAAGTAATC
      S   T   T   R   L   F   L   R   K   G   R   E   E   R   I   C   K   V   I

1021 AGCTCTCCCTGCCTGGCTGAAGCTGAAGCAAGGTTTCAGATATCATCTGAGGGTGTCACT
      S   S   P   C   L   A   E   A   E   A   R   F   Q   I   S   S   E   G   V   T

1081 GATGTCAAGGACTGAAAGCATCCTCATTTGCAGTCCACAGCATAACTTGCCAATTCAGAC
      D   V   K   D                           GTTAAC (HpaI)

1141 GAATCTCTGATCTGCTGCACTCGTGTCGGTCCCTTGTACAATCAAAATACCAGTACAGGC

1201 TTCCAGAATGCGAATGCAAATCCGTTGGAGTGTGGCACTGTCATCCTGTTGTCTTTAGGT

1261 ACCATCTAAAGTTGGCATTGTTGTAAAGTGGTAGAGCGCAAGGCTCTACTTTGTAGCCGT

1321 GGATTCGAGCCCTATGGTGGGCGTTATTTAATTTTTTTGGCGAAAAAGCCTTTAATTGAG

1381 TTGTTTAGGTGATATGAATAACTCTTTAGGTCATGGAGTTCGACTCCATGGGAGTTTAAG

1441 CTGGGTTAAAAAAAAATTATGGTCACGATCTTTTTCACATGGGCTACTGTAACATCTCGTC
```

TABLE II-continued

FULL LENGTH cDNA AND CORRESPONDING AMINO ACID SEQUENCE FOR ZmRAD51B

LOCUS ZmRAD51B (Sequence corresponding to cDNA insert in PHP7983)
FEATURES peptide from 53 to 1072
ORIGIN *Zea mays* A632 line

```
1501  TACTCCTGAACCGATGTTAAGCTTTTTAGGACTATAGATCATCTTCATATATCAACAAAA

1561  AAAAAAAAAAAAA
```

TABLE III

RAD51A SEQUENCE-SPECIFIC PROBE FRAGMENT

```
                                                         5'-CCA
TACCTGCTTT ACAGGCATCT TCAGATCCAT TGGTCTGCTA TTTGCTTTGT CATTCCTTGG

GCCAACTTTC GTGTTGCCTC ACCTTGATGT ACAAAACGGT TTCGTTCACA TATGTGAATG

CACGCCTGTG ACTGATTTAG GCGTCCTGTT GTAAATAAAA CGATGCCTGT TGCCCTGTTG

TGTGTTGCAT GTAATCGACA ACTCTACATA TCACAATTAT GATGTATTTT AGGTTTTATT

GTTCGCTTAG CACAGCCATT GCTGGATGTG CAATGTGGGA TTATAGACAA GAATCCACAC

AACAACAATG GCCAATCCTG ATAAAGTAGT TAGTGACTTG GGCAAATAGC ATTGTGGTGA

TCTTTGAGTT CACTTGTGAT AAGAACAGGG CTGGTGGCTG GTGGTGAAAA CTAACTTGTG

ATCGGAACAG GTTTAATAGG GAAAACTAAG GATTCTATAA AAAAAAAAAT AAAAAAAAAA

AAAAAAAACT CGAGGGGGGG CCCGGTACCC AATTCGCCCT ATAGTGAGTG AGTCGTATTA

CAATTCACTG GCCGTCGTTT TACAACGTCG TGACTGGGA-3'
```

TABLE IV

RAD51B SEQUENCE-SPECIFIC PROBE FRAGMENT

```
              5'-CA TCCTCATTTG CAGTCCACAG CATAACTTGC CAATTCAGAC

GAATCTCTGA TCTGCTGCAC TCGTGTCGGT CCCTTGTACA ATCAAAATAC CAGTACAGGC

TTCCAGAATG CGAATGCAAA TCCGTTGGAG TGTGGCACTG TCATCCTGTT GTCTTTAGGT

ACCATCTAAA GTTGGCATTG TTGTAAAGTG GTAGAGCGCA AGGCTCTACT TTGTAGCCGT

GGATTCGAGC CCTATGGTGG GCGTTATTTA ATTTTTTTGG CGAAAAAGCC TTTAATTGAG

TTGTTTAGGT GATATGAATA ACTCTTTAGG TCATGGAGTT CGACTCCATG GGAGTTTAAG

CTGGGTTAAA AAAAATTATG GTCACGATCT TTTTCACATG GGCTACTGTA ACATCTCGTC

TACTCCTGAA CCGATGTTAA GCTTTTTAGG ACTATAGATC ATCTTCATAT ATCAACAAAA

AAAAAAAAAA AAAACTCGAG GGGGGCCCG GTACCCAATT CGCCCTATAG TGAGTGAGTC

GTATTACAAT TCACTGGCCG TCGTTTTACA ACGTCGTGAC TGGGA-3'
```

TABLE V

Polypeptide Sequence Similarities Between ZmRAD51A And ZmRAD51B and RAD51 Homologs From Other Higher Eukaryotes

| SOURCE OF RAD51 SEQUENCE | ZmRAD51A % similarity | ZmRAD51A % identity | ZmRAD51B % similarity | ZmRAD51B % identity |
|---|---|---|---|---|
| ZmRAD51A | 100.00 | 100.00 | 94.12 | 90.00 |
| ZmRAD51B | 94.12 | 90.00 | 100.00 | 100.00 |
| Tomato | 92.65 | 86.76 | 94.12 | 89.12 |
| Human | 83.00 | 70.00 | 81.12 | 69.03 |
| Mouse | 82.79 | 69.40 | 81.12 | 69.03 |
| Chicken | 81.60 | 68.84 | 80.53 | 68.73 |

TABLE VI

| MARKER | DISTANCE | ALIAS | BIN |
|---|---|---|---|
| P1057A | 23.8 | bn1 15.40 | 7.01/7.02 |
| P1158A | 13.8 | umc98 | 7.02 |
| P9112A | 12.2 | npi112 | 7.02 |
| P1054A | 29.2 | bn1 15.21 | 7.03 |
| P1157A | 1.5 | umc110 | 7.03 |
| P1147A | 7.7 | umc56 | |
| P5533A | 15.3 | jc629 | |
| P9263A | 13.1 | npi263 | 7.04 |
| P9240A | 6.2 | npi240 | 7.04 |
| P8057A | 2.1 | rad51A | |
| P1173A | 3.1 | umc125B | 7.04 |
| P1033A | 20.9 | bn18.32 | 7.04 |
| P1036A | 3.4 | bn18.39 | 7.05 |
| P5564A | 3.6 | jc943 | |
| P554A | 22.9 | jc878 | |
| P3871A | 4.5 | umc151 | 7.05 |
| P1059A | 23.1 | bn116.06 | 7.05 |
| P1037A | 12.7 | bn18.44 | 7.06 |
| P1129A | 10.1 | umc35 | 7.06 |

TABLE VII

| MARKER | DISTANCE | ALIAS | BIN |
|---|---|---|---|
| P1035A | 25.3 | bn18.35 | 3.03 |
| P1152A | 0.0 | umc10 | |
| P8058A | 5.4 | rad51B | |
| P1044A | 10.6 | bn110.24 | 3.06 |
| P1123A | 7.1 | umc60 | 3.06 |
| P1102A | 3.2 | umc82 | |
| P1017A | 10.7 | br16.16 | 3.07 |
| P1185A | 0.0 | umc17 | 3.07 |
| P9257A | 16.3 | npi257 | 3.07 |
| P1140a | 19.2 | umc63 | 3.08 |
| P9457A | | npi457 | 3.09 |

What is claimed is:

1. An isolated polynucleotide comprising a member selected from the group consisting of:
   a) a polynucleotide encoding a polypeptide selected from the group consisting of SEQ ID NO: 3 and SEQ ID NO: 7;
   b) a polynucleotide having at least 90% identity to a polynucleotide of (a);
   c) a polynucleotide which will hybridize under stringent hybridization conditions to said polynucleotide of (a) or (b); and
   d) a polynucleotide comprising at least 30 contiguous nucleotides from a polynucleotide of (a), (b) or (c);

wherein the polynucleotide of (a), (b) or (c) encodes a polypeptide with recombinase activity.

2. The isolated polynucleotide of claim 1, wherein said polynucleotide has a sequence selected from the group consisting of SEQ ID NO: 2 and SEQ ID NO: 6.

3. An expression cassette comprising a polynucleotide of claim 1 operably linked to a promoter.

4. The host cell transfected with an expression cassette of claim 3.

5. The host cell of claim 4, wherein said host cell is a bacterial cell.

6. The host cell of claim 4, wherein said host cell is a sorghum or maize cell.

7. A method of making maize recombinase comprising the steps of:
   a) transforming or transfecting a host cell with the expression cassette of claim 3; and
   b) purifying the recombinase from the host cell.

8. The method of claim 7, wherein the host cell is selected from the group consisting of a bacterial cell, a plant cell, a mammalian cell and a yeast cell.

9. A method of modulating ZmRAD 51 activity in a plant, comprising:
   (a) introducing into a plant cell an expression cassette comprising an isolated polynucleotide of claim 1 operatively linked to a promoter;
   (b) culturing the plant cell under plant cell growing conditions;
   (c) regenerating a plant which possesses the transformed genotype, and
   (d) inducing expression of said polynucleotide for a time sufficient to modulate ZmRAD51 activity in said plant.

10. A transgenic plant cell comprising an isolated polynucleotide of claim 1.

11. A transgenic plant comprising an isolated polynucleotide of claim 1.

12. A transgenic seed from the transgenic plant of claim 11.

13. Primer pairs for isolating at least a part of a *Zea mays* recombinase gene, selected from the group consisting of SEQ ID NOS: 12 and 13, SEQ ID NOS: 14 and 19, SEQ IDS NOS: 14 and 20, and SEQ ID NOS: 14 and 15, or complements thereof.

14. An RFLP probe for a maize recombinase gene comprising at least 30 nucleotides residues of SEQ ID NO: 4, SEQ ID NO: 8, SEQ ID NO: 9, SEQ ID NO: 10, or SEQ ID NO: 11.

* * * * *